US009520054B2

(12) United States Patent (10) Patent No.: US 9,520,054 B2
Rossi et al. (45) Date of Patent: Dec. 13, 2016

(54) MOBILE USER INTERFACE FOR SMART-HOME HAZARD DETECTOR CONFIGURATION

(71) Applicant: Google Inc., Mountain View, CA (US)

(72) Inventors: Shiney Rossi, Mountain View, CA (US); Timo A. Bruck, Mountain View, CA (US); David Sloo, Menlo Park, CA (US); Jesse W. Boettcher, San Jose, CA (US); Jeffrey A. Boyd, Novato, CA (US); James B. Simister, San Francisco, CA (US)

(73) Assignee: Google Inc., Mountain View, CA (US)

(*) Notice: Subject to any disclaimer, the term of this patent is extended or adjusted under 35 U.S.C. 154(b) by 0 days.

(21) Appl. No.: 14/508,430

(22) Filed: Oct. 7, 2014

(65) Prior Publication Data

US 2015/0097682 A1 Apr. 9, 2015

Related U.S. Application Data

(60) Provisional application No. 61/887,963, filed on Oct. 7, 2013, provisional application No. 61/887,969, filed on Oct. 7, 2013.

(51) Int. Cl.
*G08B 29/26* (2006.01)
*G08B 21/18* (2006.01)
(Continued)

(52) U.S. Cl.
CPC .......... *G08B 29/26* (2013.01); *F24F 11/0009* (2013.01); *G01N 27/02* (2013.01); *G01N 27/121* (2013.01);
(Continued)

(58) Field of Classification Search
CPC ..... G08B 17/10; G08B 17/117; G08B 25/008; G08B 25/012; G08B 21/182; G08B 21/18; G08B 21/12; G08B 29/185
See application file for complete search history.

(56) References Cited

U.S. PATENT DOCUMENTS 4,651,020 A * 3/1987 Kenny .................. H02J 9/061
307/43
5,155,468 A * 10/1992 Stanley .................. H04Q 9/14
340/501

(Continued)

FOREIGN PATENT DOCUMENTS

JP 2010236759 A * 10/2010

*Primary Examiner* — Hongmin Fan
(74) *Attorney, Agent, or Firm* — Kilpatrick Townsend & Stockton LLP

(57) ABSTRACT

System for displaying hazard events and adjusting hazard detector settings on a mobile device includes a user interface executed on the mobile device, a hazard detector, and a computer server system communicatively coupled to the mobile device and hazard detector. The hazard detector generates hazard events indicating detection of smoke or carbon monoxide. The hazard events are transmitted to the computer server system and then to the mobile device. User interface displays the hazard events in an event group. User interface receives an adjusted value for a setting of the hazard detector and transmits the adjusted value to the computer server system. The computer server system determines that the adjusted value corresponds to the hazard detector, receives a check-in event from the hazard detector, and transmits the adjusted value to the hazard detector in response to receiving the check-in event. The hazard detector applies the adjusted value to the setting.

20 Claims, 22 Drawing Sheets

(51) Int. Cl.
  *G08B 17/10*   (2006.01)
  *G01N 27/02*   (2006.01)
  *G01N 27/12*   (2006.01)
  *G01N 33/00*   (2006.01)
  *G08B 17/117*  (2006.01)
  *G08B 25/00*   (2006.01)
  *G08B 29/18*   (2006.01)
  *G08B 5/36*    (2006.01)
  *G08B 3/10*    (2006.01)
  *G08B 21/14*   (2006.01)
  *H04L 12/28*   (2006.01)
  *G08B 5/22*    (2006.01)
  *G08B 21/12*   (2006.01)
  *F24F 11/00*   (2006.01)
  *G08B 25/01*   (2006.01)
  *G08B 29/02*   (2006.01)
  *G08B 29/04*   (2006.01)
  *G08B 25/08*   (2006.01)

(52) U.S. Cl.
  CPC ........ *G01N 33/004* (2013.01); *G01N 33/0031* (2013.01); *G08B 3/10* (2013.01); *G08B 5/22* (2013.01); *G08B 5/36* (2013.01); *G08B 17/10* (2013.01); *G08B 17/117* (2013.01); *G08B 21/12* (2013.01); *G08B 21/14* (2013.01); *G08B 21/18* (2013.01); *G08B 21/182* (2013.01); *G08B 25/002* (2013.01); *G08B 25/008* (2013.01); *G08B 25/012* (2013.01); *G08B 29/02* (2013.01); *G08B 29/04* (2013.01); *G08B 29/185* (2013.01); *H04L 12/2803* (2013.01); *H04L 12/2818* (2013.01); *G08B 25/08* (2013.01)

(56) References Cited

U.S. PATENT DOCUMENTS

| | | | | |
|---|---|---|---|---|
| 6,100,792 A   | * | 8/2000  | Ogino     | B60R 25/1001 340/12.54 |
| 8,170,722 B1  | * | 5/2012  | Elberbaum | H04L 12/281 455/151.1 |
| 2002/0095078 A1 | * | 7/2002 | Mannheimer | A61B 5/14552 600/323 |
| 2004/0227064 A1 | * | 11/2004 | Linge    | H05B 37/0209 250/221 |
| 2005/0125081 A1 | * | 6/2005 | Ota       | G08C 17/02 700/17 |
| 2008/0016440 A1 | * | 1/2008 | Liu       | H04L 41/0266 715/700 |
| 2011/0018726 A1 | * | 1/2011 | Gonzales  | G08B 29/185 340/628 |
| 2012/0011466 A1 | * | 1/2012 | Miyamoto  | G06F 3/0485 715/786 |
| 2012/0158161 A1 | * | 6/2012 | Cohn      | H04L 12/2827 700/90 |
| 2013/0328697 A1 | * | 12/2013 | Lundy    | G08C 17/02 340/870.16 |
| 2014/0076969 A1 | * | 3/2014 | Marshall Chesney | G07C 9/00103 235/382 |
| 2014/0277748 A1 | * | 9/2014 | Dyess     | G05B 15/02 700/275 |

* cited by examiner

FIG. 20

MOBILE USER INTERFACE FOR SMART-HOME HAZARD DETECTOR CONFIGURATION

CROSS-REFERENCES TO RELATED APPLICATIONS

This application claims the benefit of U.S. Provisional Patent Application No. 61/887,963, filed Oct. 7, 2013, entitled "HAZARD DETECTION IN A SMART-SENSORED HOME," and U.S. Provisional Patent Application No. 61/887,969, filed Oct. 7, 2013, entitled "USER-FRIENDLY DETECTION UNIT," the entire disclosures of which are hereby incorporated by reference for all purposes.

BACKGROUND

1. The Field of the Invention

The present invention generally relates to hazard detection. More specifically, the present invention relates to a mobile user interface for network connected hazard detection units.

2. The Relevant Technology

Hazard detectors use a variety of sensors to detect substances in the air that are harmful or indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming a user. In other instances, a substance such as smoke, while not necessarily harmful in and of itself, can indicate the development of a hazardous situation, such as fire. An early alarm of the presence of such a substance can prevent the hazardous situation from developing or minimize the harmful effects of the situation.

Interconnected hazard detectors are detectors that are connected to a network, enabling communication between the detectors or with a central control unit. This provides several advantages over standalone detectors, including the ability to activate multiple alarms when a single detector is triggered.

BRIEF SUMMARY

In one embodiment, a system for displaying hazard events on a mobile device remote from a detection location is presented. The system includes a hazard detector, a computer server system, and a user interface executed on the mobile device. The computer server system is communicatively coupled to the hazard detector and the mobile device.

The hazard detector is configured to detect a first hazard level that is greater than a first threshold. The first hazard level indicates an amount of smoke or carbon monoxide (CO) present at the hazard detector. A first hazard event is generated indicating the detection of the first hazard level and the hazard detector transmits the first hazard event to the computer server system via a wireless protocol. The hazard detector also detects a second hazard level that is greater than a second threshold, generates a second hazard event indicating the detection of the second hazard level, and transmits the second hazard event to the computer server system via the wireless protocol.

The computer server system is configured to store a plurality of accounts, each account being associated with at least one hazard detector. The first hazard event is received, and the computer server system determines that the hazard detector transmitted the first hazard event. The computer server system further determines that the hazard detector is associated with a first account and that the mobile device is authorized to access the first account. The first hazard event is transmitted to the mobile device. The second hazard event is received and the computer server system determines that the hazard detector transmitted the second hazard event. The computer server system transmits the second hazard event to the mobile device.

The user interface is configured to receive the first hazard event, receive the second hazard event, and display the first hazard event and the second hazard event in an event group. The event group indicates that the first hazard event and the second hazard event occurred in a chain of related events.

In another embodiment, a method is presented for displaying hazard events on a mobile device remote from a detection location. The method includes establishing a first communication link between a hazard detector and a computer server system. The first communication link includes a wireless segment wherein data is transmitted and received via a wireless protocol. A second communication link is established between the mobile device and the computer server system. A hazard level greater than a threshold is detected, the hazard level indicating an amount of smoke or CO present at the hazard detector. A light having a specific color is activated on the hazard detector. A hazard event is transmitted from the hazard detector to the computer server system via the first communication link. The hazard event indicates the detection of the hazard level. The hazard event is further transmitted from the computer server system to the mobile device via the second communication link. The specific color is displayed via a user interface executed on the mobile device.

In a further embodiment, a non-transitory computer-readable medium is presented. The computer-readable medium has instructions stored therein, which when executed cause a computer to perform a set of operations. The set of operations include receiving a hazard event generated by a hazard detector. The hazard event indicates that the hazard detector detected a hazard level greater than a threshold, the hazard level indicating an amount of smoke or CO present at the hazard detector. A status for the hazard detector is displayed including a link for the history of the hazard detector. User input selecting the link is received and a request for a history of events for the hazard detector is transmitted to a computer server system in response to receiving the user input. A plurality of historical events for the hazard detector is received as a response to the request. Each of the plurality of historical events includes a date and a time of when the historical event occurred. The plurality of historical events for the hazard detector including the date and time of each historical event is displayed.

In one embodiment, a system for adjusting a setting of a hazard detector on a mobile device remote from the hazard detector is presented. The system includes a user interface executed on the mobile device, a computer server system, and the hazard detector. The computer server system is communicatively coupled to the mobile device and the hazard detector.

The user interface is configured to display a current value for the setting of the hazard detector. The current value indicates a value for the setting that is currently in effect on the hazard detector. The user interface receives user input indicating an adjustment to the setting, the adjustment to change the setting from the current value to an adjusted value. The adjusted value is transmitted to the computer server system and a pending indicator is displayed for the setting indicating that the adjusted value is not in effect on the hazard detector. The user interface receives a signal from the computer server system indicating that the adjusted value is in effect on the hazard detector and the pending indicator is removed in response to receiving the signal.

The computer server system is configured to receive the adjusted value and determine that the adjusted value corresponds to the hazard detector. A check-in event is received from the hazard detector and the adjusted value is transmitted to the hazard detector in response to receiving the check-in event. The computer server system also transmits the signal indicating that the adjusted value is in effect to the mobile device.

The hazard detector is configured to detect smoke or CO. The hazard detector transmits the check-in event to the computer server system after a time interval since transmitting a previous check-in event. The adjusted value is received and the hazard detector applies the adjusted value to the setting.

In another embodiment, a method for adjusting a setting of a hazard detector on a mobile device remote from the hazard detector is presented. The method includes displaying a list of settings for the hazard detector. The hazard detector is configured to detect smoke or CO. A first user input selecting the setting from the list of settings is received and a display area for the setting is expanded in response to receiving the first user input. The method further includes displaying a current value for the setting in the expanded display area. The current value indicates a value for the setting that is currently in effect on the hazard detector. A second user input indicating an adjustment to the setting is received, the adjustment to change the setting from the current value to an adjusted value. The adjusted value is transmitted from the mobile device to the computer server system. A check-in event is transmitted from the hazard detector to the computer server system after transmitting the adjusted value from the mobile device to the computer server system. The adjusted value is transmitted from the computer server system to the hazard detector after transmitting the check-in event from the hazard detector to the computer server system. The adjusted value is applied to the setting on the hazard detector.

In a further embodiment, a non-transitory computer-readable medium is presented. The computer-readable medium has instructions stored therein, which when executed cause a computer to perform a set of operations. The set of operations include displaying a list of settings for a hazard detector. The hazard detector is configured to detect smoke or CO. A first user input selecting a first setting from the list of settings is received and a first display area for the first setting is expanded in response to receiving the first user input. A first current value for the first setting is displayed in the expanded first display area. The first current value indicates a value for the first setting that is currently in effect on the hazard detector.

A second user input selecting a second setting from the list of settings is received. The first display area for the first setting is reduced and a second display area for the second setting is expanded in response to receiving the second user input. A second current value for the second setting is displayed in the expanded second display area. The second current value indicates a value for the second setting that is currently in effect on the hazard detector. A third user input indicating an adjustment to the second setting is received, the adjustment to change the second setting from the second current value to an adjusted value. A pending indicator for the second setting is displayed indicating that the adjusted value is not in effect on the hazard detector. The adjusted value is transmitted to a computer server system. A signal is received from the computer server system indicating that the adjusted value for the second setting is in effect on the hazard detector and the pending indicator is removed in response to receiving the signal.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 20 is an illustration of a user interface on a mobile device displaying further adjustable settings for a hazard detector, according to an embodiment.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Interconnected hazard detectors are typically used in large buildings and complexes. In these environments, the hazard detectors are connected to a central control unit. Some jurisdictions also require interconnected hazard detectors at home, in which case the hazard detectors are connected to each other rather than a central control unit. The networking of hazard detectors in an interconnected system enables more effective automated responses. For example, when a hazard detector is triggered, a fire suppression system (e.g., a sprinkler system) at or near the triggered detector can be activated. In other instances, all of the connected detectors can activate an alarm when a single detector is triggered, or an alarm system can be activated to notify an entire building or complex of the hazardous situation.

However, although interconnected hazard systems provide more effective responses compared to standalone hazard detectors, there are still situations where even interconnected systems are not effective. For example, if no one is home when a hazardous situation develops, activating an alarm, or even multiple alarms, inside the home will not be an effective response for preventing property damage. Furthermore, as hazard detectors become more advanced and new features are added, it is inconvenient for users to press buttons on the hazard detector in order to adjust the settings of the features. This is especially true for smoke detectors, since most smoke detectors are located high up on walls or ceilings and can be difficult for users to reach.

The embodiments of the invention described herein below overcome the disadvantages of the prior art by providing methods and systems for generating a user interface on a mobile device remote from a hazard detector. The hazard detector is triggered by the presence of a hazardous substance and generates a hazard event indicating the detection of the hazardous substance. The hazard event is transmitted to a computer server system. The computer sever system determines a mobile device associated with the triggered hazard detector and transmits the hazard event to the mobile device. A user interface is executed on the mobile device for displaying the hazard event. The user interface can also be used to adjust the settings of the hazard detector.

Figure 1:
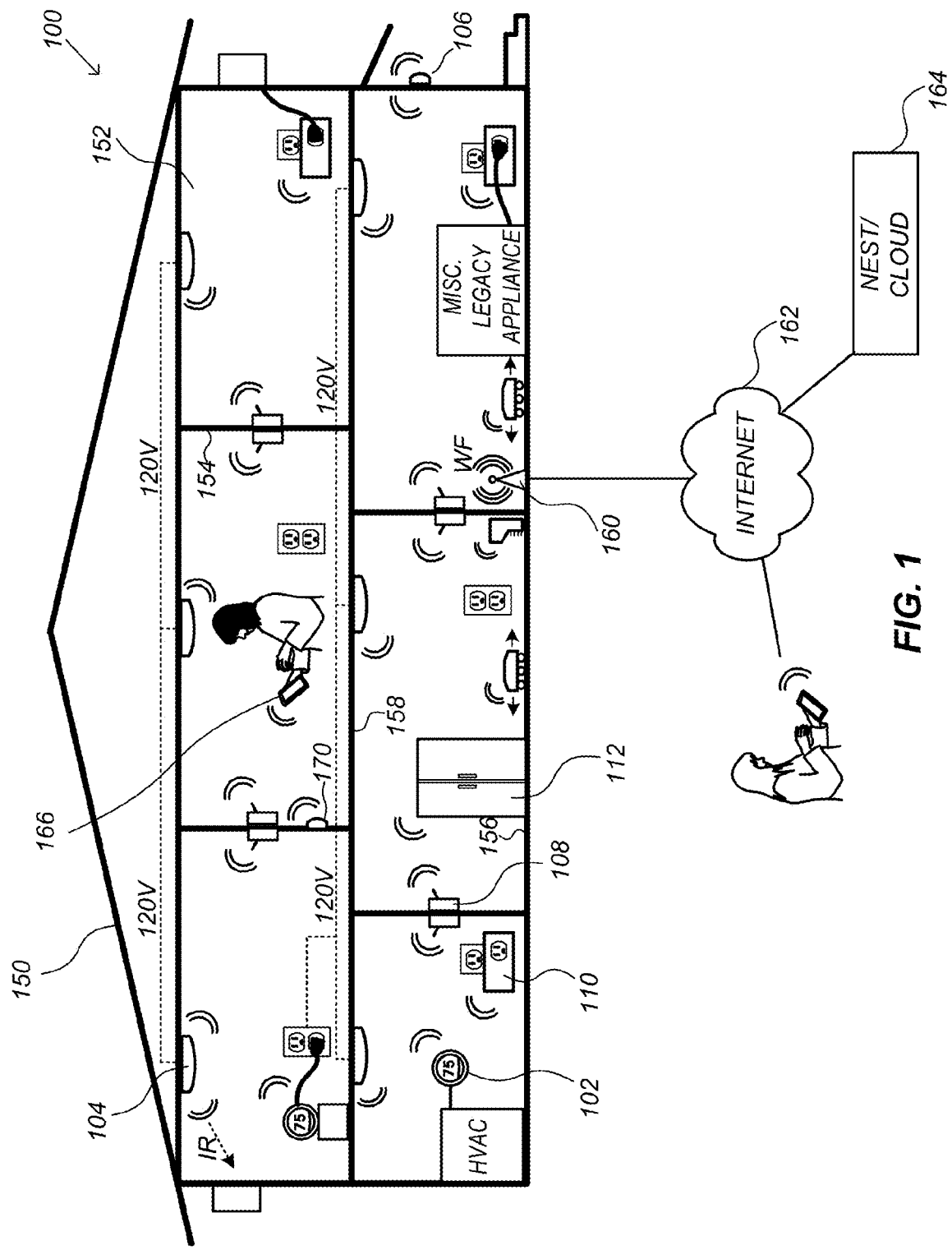
FIG. 1 is an example of a smart-home environment within which one embodiment of a system for generating a user interface on a mobile device remote from a hazard detector can be implemented.

FIG. 1 is an example of a smart-home environment 100 within which one embodiment of a system for generating a user interface on a mobile device remote from a hazard detector can be implemented. The depicted smart-home environment 100 includes an enclosure 150, which can be, e.g., a house, office building, hotel, retail store, garage, or mobile home. The system can also be implemented in a smart-home environment 100 that does not include an entire enclosure 150, such as an apartment, condominium, or office space.

The depicted enclosure 150 includes a plurality of rooms 152, separated at least partly from each other via walls 154. The walls 154 can include interior walls or exterior walls. Each room can further include a floor 156 and a ceiling 158. Devices can be mounted on, integrated with and/or supported by a wall 154, floor 156 or ceiling 158. Further, the smart home environment can include devices outside of the actual enclosure 150, such as a pool heater or irrigation system.

The smart-home environment 100 includes a plurality of intelligent, multi-sensing, network-connected devices (hereinafter referred to as "the smart devices") that can integrate seamlessly with each other and with a computer server system 164, such as a cloud-computing system. The smart devices can include smart thermostats 102, smart hazard detectors 104, smart entryway devices 106 (e.g., doorbells or intercoms), smart wall switches 108, smart wall plug interfaces 110, and smart appliances 112, such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth.

Any of the smart devices in the smart-home environment can include any number of sensors. For example, smart appliances 112 can include sensors that detect when they are being used. Additionally, a motion or occupancy sensor, such as an ultrasonic, passive infrared (PIR), or optical sensor, can be included in any of the smart devices to detect user activity and movement. Some smart devices will also have sensors specific to the device. For example, a smart light can include an ambient light sensor, such as a photoresistor or a single-pixel sensor that measures light in the room. Smart hazard detectors 104 can include smoke/fire/heat sensors, carbon monoxide/dioxide sensors, radon gas detectors, ambient light sensors, temperature sensors, humidity sensors, and the like. Any smart device can also include a processor for processing data from the sensors or other devices.

Each smart device is also equipped with communications ports or transceivers for communicating data with other smart devices. In one embodiment, the devices establish a mesh network for communication between devices. In another embodiment, the devices can connect, via a router or gateway 160, to a private network or the internet 162, including any computer server system 164 and computing device that is connected to the same network. Data can be transferred via any wireless (e.g., Wi-Fi, ZigBee, 6LoW-PAN, etc.) or wired (CAT6 Ethernet, HomePlug, etc.) protocols.

By virtue of network connectivity, one or more of the smart devices can further allow a user to interact with the device even if the user is not proximate to the device. For example, a user can communicate with a device using a computer (e.g., a desktop computer) or mobile device (e.g., a smartphone, laptop computer, or tablet) 166. A webpage or native mobile app can be configured to receive input from the user and control the device based on the input. The webpage or mobile app can also present information about the device's operation to the user. For example, the user can view the status of a smart hazard detector or a history of notifications generated by the smart hazard detector. The user can be in the enclosure during this remote communication or outside the enclosure.

Figure 2:
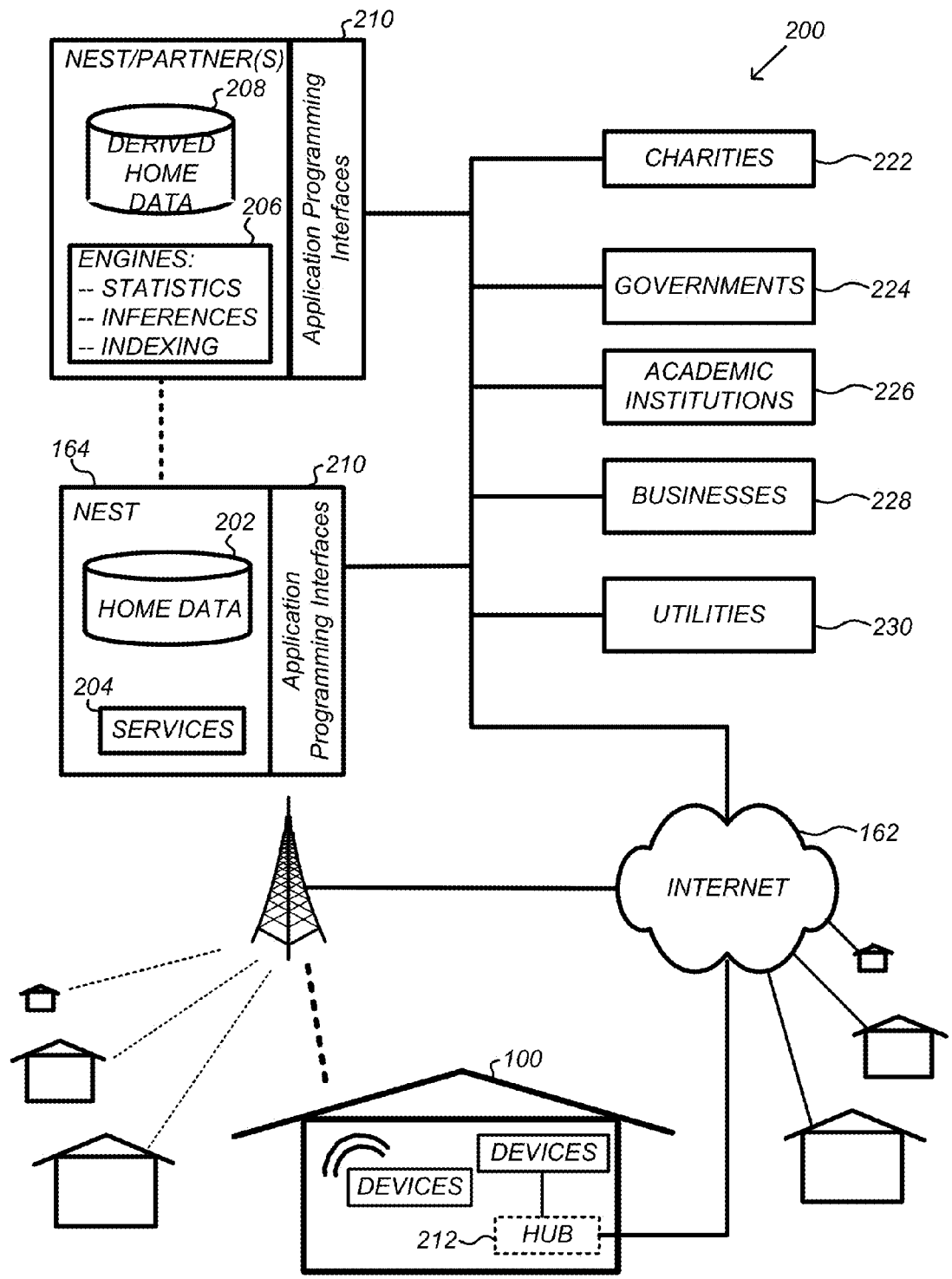
FIG. 2 is a network-level view of one embodiment of a system for generating a user interface on a mobile device remote from a hazard detector.

FIG. 2 is a network-level view of one embodiment of a system 200 for generating a user interface on a mobile device remote from a hazard detector. System 200 includes computer server system 164. Smart devices can communicate with the computer server system 164 via a private network or the internet 162. Smart devices can transmit home data 202, including user data and user activity data, to computer server system 164 for processing or storage. More specifically, home data 202 can include power consumption data, occupancy data, HVAC settings and usage data, carbon monoxide levels data, smoke levels data, volatile organic compounds levels data, sleeping schedule data, cooking schedule data, inside and outside temperature humidity data, television viewership data, inside and outside noise level data, etc.

The computer server system 164 can further provide one or more services 204. The services 204 can include customized hazard notifications, software updates, customer support, sensor data collection/logging, remote access, remote or distributed control, or use suggestions (e.g., based on collected home data 202 to improve performance, reduce utility cost, etc.). To facilitate these services, users can register the smart devices in their home or enclosure with the computer server system 164. Computer server system 164 can associate the smart devices with an account during the registration process. The account can be user specific or specific to a home or enclosure that includes multiple users, and a unique identification of each smart device can be stored in the account. In one embodiment, the user's mobile device or other computing device can also be associated with the account during registration. In another embodiment, one or more username and password is associated with the account during registration. The user can then use the username and password to log in on the mobile or computing device, and computer server system 164 can use the account to authorize the user's mobile or computing device for the services 204. Any identifying information can be used to log in and authorize users and their computing devices. For example, the mobile or computing device can include a fingerprint scanner, and the user logs in using their fingerprint. Data associated with the services 204, such as account data, can be stored at the computer server system 164.

System 200 includes a processing engine 206, which can be concentrated at a single server or distributed among several different computing entities without limitation. A single server can also include multiple engines for performing different processing tasks. The processing engine 206 can receive data from smart devices, index and store the data, or process the data to generate customized notifications or statistics. The processed data can be stored as derived home data 208. Results of the processing can be transmitted back to the device that provided the home data, to other devices, to a server providing a webpage to a user of the device, or to other non-device entities. For example, hazard events generated by smart hazard detectors can be received and processed by the processing engine 206 before being transmitted to a user device via the Internet 162. In this manner, the processing engine 206 can be configured and programmed to derive a variety of useful information from the home data 202.

In some embodiments, to encourage innovation and research and to increase products and services available to users, system 200 provides application programming interfaces (APIs) 210 to third parties, such as charities 222, governmental entities 224 (e.g., emergency response units such as a fire department or police department, the Food and Drug Administration, or the Environmental Protection Agency), academic institutions 226 (e.g., university researchers), businesses 228 (e.g., security or fire monitoring service providers, social network providers, device warranty or equipment service providers, or providers of targeted advertisements based on home data), utility companies 230, and other third parties. The APIs 210 permit third-party systems to communicate with the computer server system 164, providing access to the services 204, the processing engine 206, the home data 202, and the derived home data 208. This allows third-party applications to submit specific data processing tasks to the computer server system 164 and receive dynamic updates to the home data 202 and the derived home data 208. For example, a fire department or fire monitoring service provider can develop applications using the APIs 210 to provide emergency response services to users.

In other embodiments, the services 204 can utilize third-party APIs to communicate with third-party applications. For example, if a smart hazard detector is triggered, a hazard event can be transmitted to an emergency response system, such as one provided by a fire department, using an API of the emergency response system. Third-party APIs can also be used to collect user data and user activity data from third-parties. For example, an API of a social network provider can be utilized to gather user activity data for a user.

Figure 3:
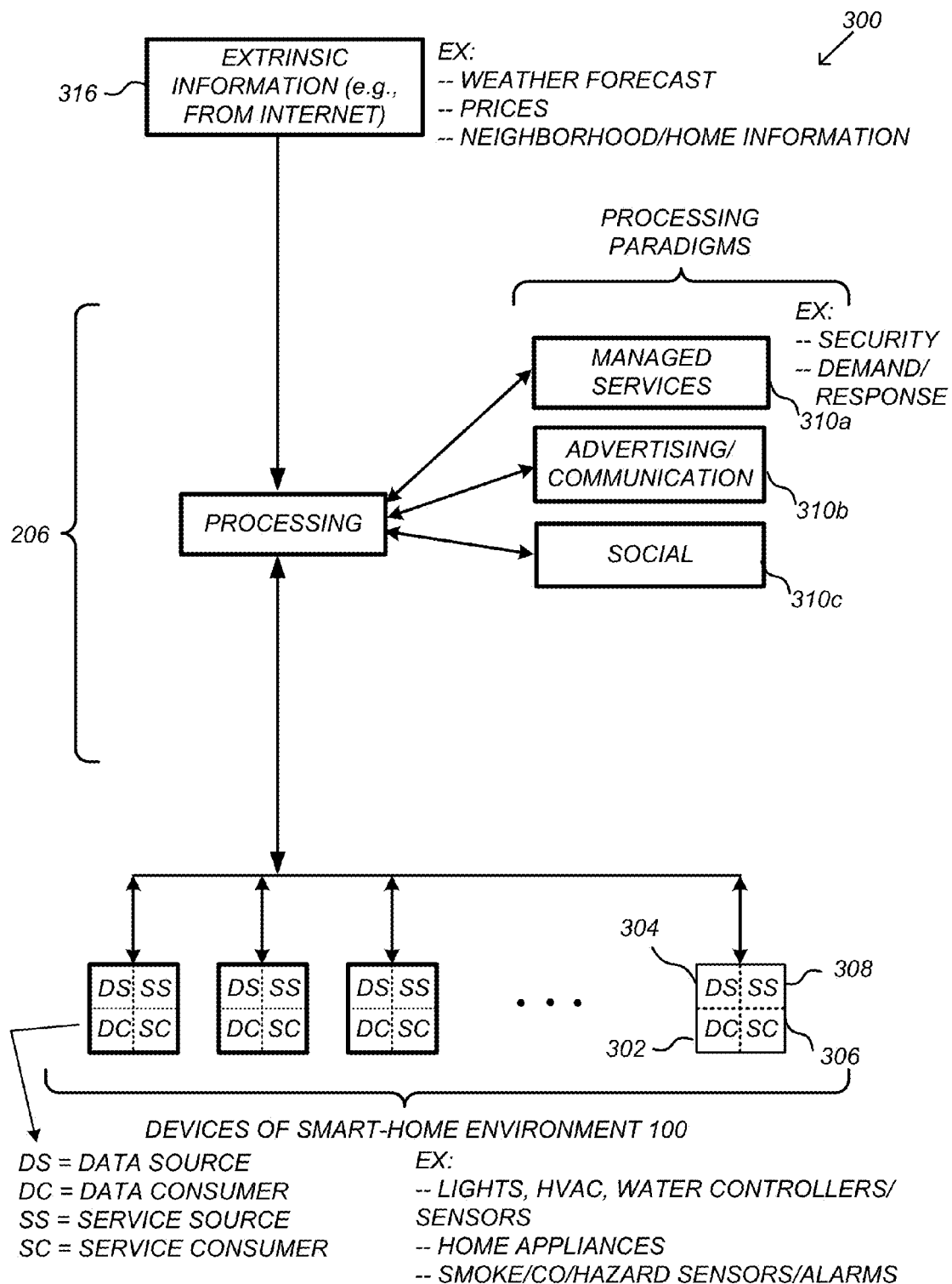
FIG. 3 is an abstracted functional view of one embodiment of a system for generating a user interface on a mobile device remote from a hazard detector.

FIG. 3 is an abstracted functional view of one embodiment of a system 300 for generating a user interface on a mobile device remote from a hazard detector. Smart devices, such as those of the smart-home environment 100 of FIG. 1, share common characteristics in that each smart device is a data consumer 302 (DC), a data source 304 (DS), a services consumer 306 (SC), and a services source 308 (SS). System 300 can be configured to harness the large amount of data generated by the smart devices to provide a variety of automated, extensible, flexible, and/or scalable technologies for achieving useful objectives. These objectives may be predefined or adaptively identified based on, e.g., user activity data or user input.

System 300 includes processing engine 206, which further includes a number of paradigms 310. Processing engine 206 can include a managed services paradigm 310a that monitors and manages device functions, such as ensuring proper operation of a device, responding to emergency situations, or detecting failure of equipment coupled to the device (e.g., a burned out light bulb). Processing engine 206 can further include an advertising/communication paradigm 310*b* that identifies characteristics (e.g., demographic information) of a user or products of interest to a user based on device usage. Processing engine 206 can further include a social paradigm 310*c* that collects data from and transmits data to a social network. For example, a user's status as reported on the social network can be collected and processed to determine user activity.

The processing engine 206 can also utilize extrinsic information 316 with the processing paradigms. Extrinsic information 316 can be used to interpret data received from a smart device, to determine a characteristic of the environment near the smart device (e.g., outside an enclosure that contains the smart device), to determine services or products available to the user, to identify a social network or social-network information, to determine contact information of entities (e.g., public service entities such as an emergency response team, the police or a hospital) near the smart device, or to identify statistical or environmental conditions, trends or other information associated with a home or neighborhood.

Figure 4:
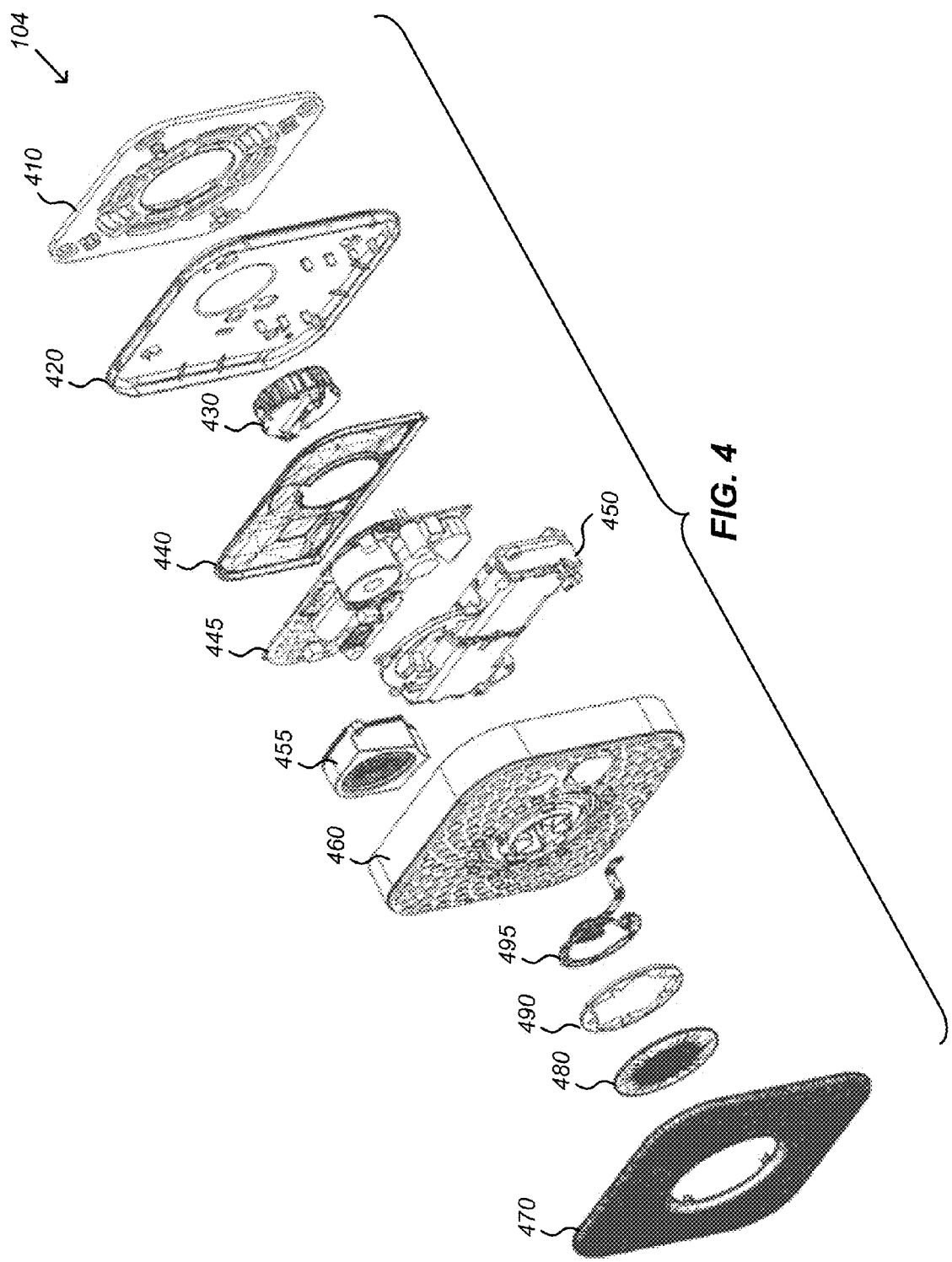
FIG. 4 is an illustration of an exploded perspective view of a smart hazard detector that is included in an embodiment of a system for generating a user interface on a mobile device remote from the hazard detector.

FIG. 4 is an illustration of an exploded perspective view of a smart hazard detector 104 that is included in an embodiment of a system for generating a user interface on a mobile device remote from the hazard detector 104. Hazard detector 104 can include a smoke detector, carbon monoxide detector, heat detector, and humidity sensor. Hazard detector 104 is configured to sound an audible notification, such as an alarm, when a sufficient level (e.g., above a threshold setting) of smoke or some other hazardous substance is detected. In one embodiment, hazard detector 104 also includes other sensors such as a motion sensor or ambient light sensor. Hazard detector 104 can also include a wireless transceiver for transmitting data, e.g., when a hazardous substance or user activity is detected, to other smart devices or a computer server system.

In one embodiment, hazard detector 104 is a roughly square or rectangular shaped object having a width of approximately 120 to 134 mm and a thickness of approximately 38 mm. Hazard detector 104 includes a mounting plate 410 that can be attached to a wall or ceiling and a back plate 420 that can be mounted to the mounting plate 410. Hazard detector 104 further includes a front casing 460 that can be secured to the back plate 420 to define a housing with an interior region for containing the components of the hazard detector 104.

A circuit board 445 can be attached to the back plate 420 and various components can be mounted to the circuit board 445. For example, a smoke chamber 430 can be mounted on circuit board 445 and configured to detect the presence of smoke. In one embodiment, smoke chamber 430 can be mid-mounted relative to circuit board 445 so that air can flow into smoke chamber 430 from above the circuit board 445 and below the circuit board 445. A speaker 455 and alarm device (not numbered) can also be mounted on circuit board 445 to audibly warn an occupant of a potential fire danger when the presence of smoke is detected in the smoke chamber 430. Other components, such as a motion sensor (e.g., ultrasonic, passive IR, etc.), carbon monoxide sensor, temperature sensor, heat sensor, ambient light sensor, noise sensor, microprocessor, and the like may likewise be mounted on circuit board 445.

In one embodiment, a protective plate 440 can be attached to circuit board 445 to provide a visually pleasing appearance to the inner components of hazard detector 104 or to funnel airflow to smoke chamber 430. For example, when a user views the internal components of hazard detector 104, such as through the vents in back plate 420, protective plate 440 can provide the appearance of a relatively smooth surface and otherwise hide the components or circuitry of circuit board 445. Protective plate 440 can likewise function to direct air flow from the vents of back plate 420 toward smoke chamber 430.

Hazard detector 104 can also include a battery pack 450, which can be the main source of power for the various components of hazard detector 104. In one embodiment, battery pack 450 is a backup power source and hazard detector 104 is further coupled with a primary external power source, such as a 120 V power source of the home or enclosure. In some embodiments, a cover plate 470 can be attached to the front casing 460 to provide a visually pleasing appearance or for other functional purposes. In a specific embodiment, cover plate 470 may include a plurality of holes or openings so that the sensors on circuit board 445 can detect external objects. The plurality of openings can be arranged to provide a visually pleasing appearance when viewed. For example, the openings can be arranged according to a repeating pattern, such as a Fibonacci or other sequence.

A lens button 480 can be coupled with or otherwise mounted to cover plate 470. Lens button 480 can be transparent, allowing the sensors to view through the lens button 480. For example, a PIR sensor (not shown) can be positioned behind the lens button 480 to detect the activity or movement of a user. In some embodiments, lens button 480 can also function as a pressable button for inputting commands, such as to shut off a false alarm. A light ring 490 can be positioned distally behind lens button 480. The light ring 490 can be configured to receive and disperse light, e.g., from an LED or other light source, so as to provide a desired visual appearance, such as a halo, behind the lens button 480. A flexible circuit board 495 that includes one or more electrical components, such as a PIR sensor or LEDs, can be positioned behind the light ring 490. Flexible circuit board 495 can be electrically coupled to circuit board 445, enabling data communications with one or more microprocessors mounted on circuit board 445.

Figure 5:
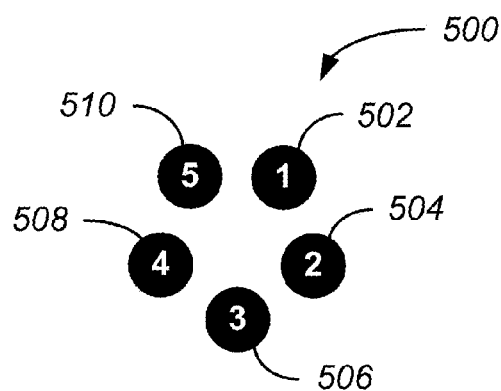
FIG. 5 is an illustration of the arrangement pattern of LED lights on a hazard detector, according to an embodiment.

FIG. 5 is an illustration of the arrangement pattern of LED lights on a hazard detector, according to an embodiment. This representation includes five light elements 502, 504, 506, 508 and 510. Light elements 500 may be turned on and off according to a number of patterns and each may cycle through different hue ranges. The color of each light element may also vary in order to provide an additional variety of visual effects.

Figure 6:
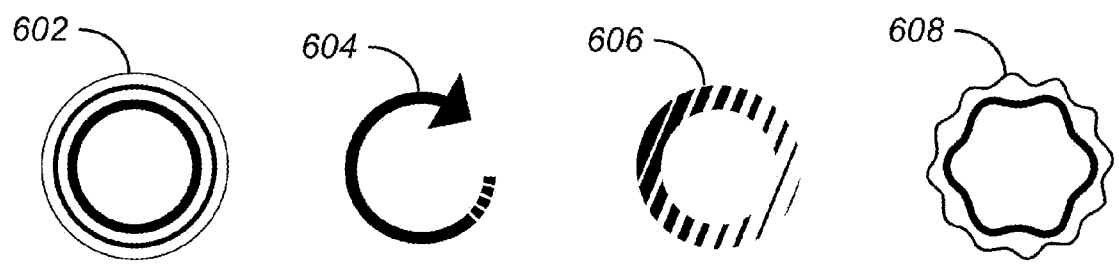
FIG. 6 is an illustration representing four different visual effects that can be generated by a hazard detector, according to an embodiment.

FIG. 6 is an illustration representing four different visual effects that can be generated by a hazard detector, according to an embodiment. Visual effect 602 is a representation of a pulsing effect that may be created when all of lights elements 502, 504, 506, 508 and 510 (shown in FIG. 5) are turned on and off simultaneously. Alternatively, all of light elements 502, 504, 506, 508 and 510 may increase and decrease the brightness of the light produced in a synchronized fashion to create a pulsing effect.

Visual effect 604 represents a rotating effect that can be created when all of light elements 502, 504, 506, 508 and 510 are turned on and off sequentially in a clockwise direction. In one embodiment, turning on and off the lights can be done in a gradual fashion. For example, light element 504 can gradually turn off and light element 502 gradually turns on while light elements 506, 508 and 510 are turned on at an equal brightness.

Visual effect 608 represents a wave visual effect that can be created when light elements 500 (shown in FIG. 5) turn on and off in a side-to-side direction. For example, at a given point in time, light element 510 is the brightest, light elements 508 and 502 are the next brightest, and light elements 506 and 504 are the least bright. Shortly thereafter, the lights may gradually change brightness in a linear manner such that light elements 504 and 506 are the brightest, lights 508 and 502 are the next brightest, and light 510 is the least bright.

Visual effect 610 represents a shimmer visual effect that can be created when each of the light elements 500 cycle through a hue range pattern, with each light element's hue range pattern being out of sync with all the other lights.

Figure 7:
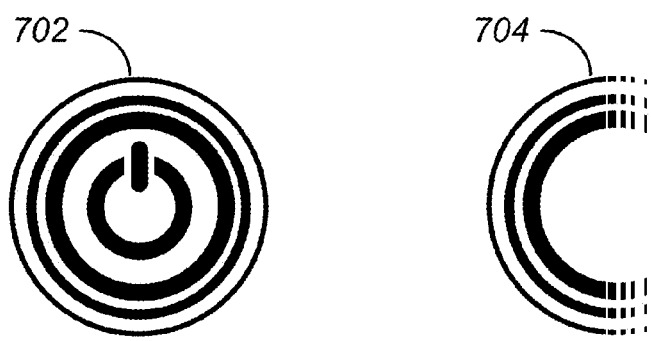
FIG. 7 is an illustration representing variations of a pulse visual effect that can be generated by a hazard detector, according to an embodiment.

FIG. 7 is an illustration representing variations of a pulse visual effect that can be generated by a hazard detector, according to an embodiment. Visual effect 702 represents an on and off pattern for power off or no power available situations wherein the pulse animations will transition smoothly through pulses in order to provide an alert in a non-distracting manner. Visual effect 704 represents a left-to-right pulse pattern that could be used when presenting a user with selectable options via visual effects. For example, a button can be used to select a language preference for the operation of a hazard detector during initial setup. The user can be asked to press the button when the left side is pulsing for English and when the right side is pulsing for Chinese.

Figure 8:
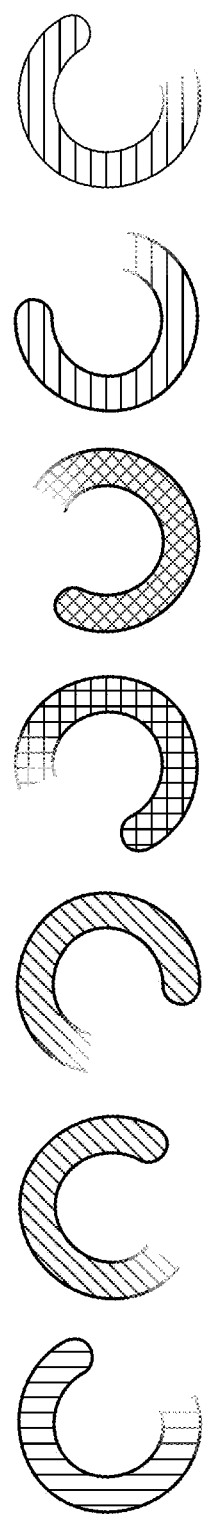
FIG. 8 is an illustration of a rotating visual effect that can be generated by a hazard detector, according to an embodiment.

FIG. 8 is an illustration of a rotating visual effect that can be generated by a hazard detector, according to an embodiment. FIG. 8 provides a further illustration of the rotating visual effect 604 of FIG. 6. Viewed from left to right, FIG. 8 shows new lights turning on at one end of the rotating visual effect and other lights gradually turning off at the other end of the rotating visual effect. The hatch patterns of each of the sequential representations illustrate how the rotating light may change color during the rotation sequence. Although light elements 502, 504, 506, 508 and 510 may each be a different color individually, the colored light mixing causes the color of the rotating visual effect to constantly change during the course of the visual effect.

Figure 9:
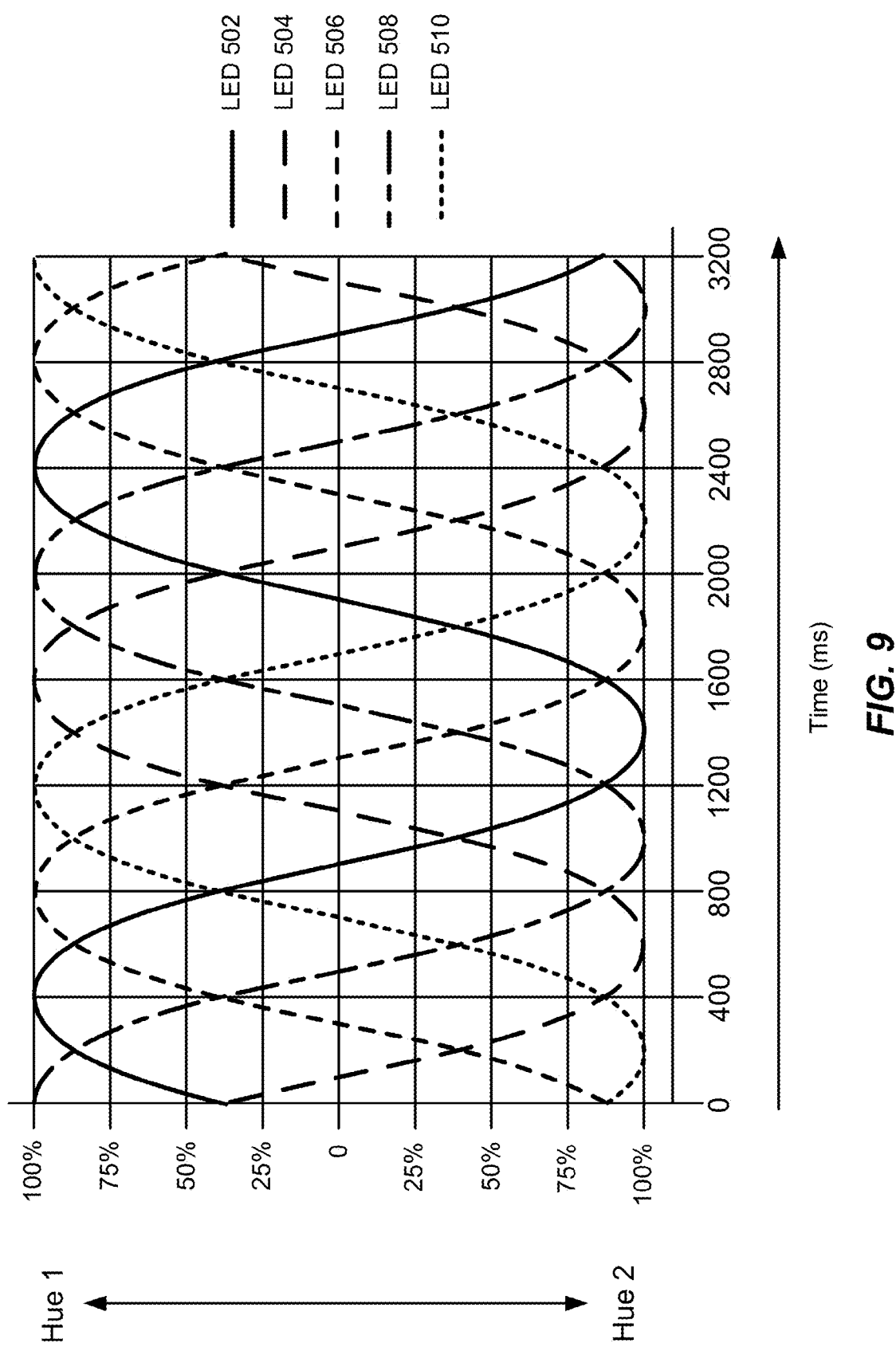
FIG. 9 is an illustration of the different hue range patterns associated with each of the light elements for a shimmering visual effect that can be generated by a hazard detector, according to an embodiment.

FIG. 9 is an illustration of the different hue range patterns associated with each light element for a shimmering visual effect that can be generated by a hazard detector, according to an embodiment. The extent to which the lights 502, 504, 506, 508 and 510 are out of sync may be varied in order to produce variations of the shimmering visual effect.

In various embodiments, the visual effects described above can be varied in a number of different ways. For example, each effect may be animated faster or slower, brighter or dimmer, for a specific number of animation cycles, with only some of the light participating, and using different colors, e.g., white, blue, green, yellow and red. These visual effects can be generated by a hazard detector for a variety of purposes. For example, a specific color, animation, animation speed, etc. or combinations thereof can represent one or more of the following alerts or notifications provided by a hazard detector: booting up, selecting language, ready for connections, connected to client, button pressed, button pressed for test, countdown to test, test under way, test completed, pre-alarms, smoke alarms, carbon monoxide alarms, heat alarms, multi-criteria alarms, hushed after alarm, post-alarm, problems, night light state, reset, shutdown begin, shutdown, safely light, battery very low, battery critical, power confirmation, and more.

Figure 10:
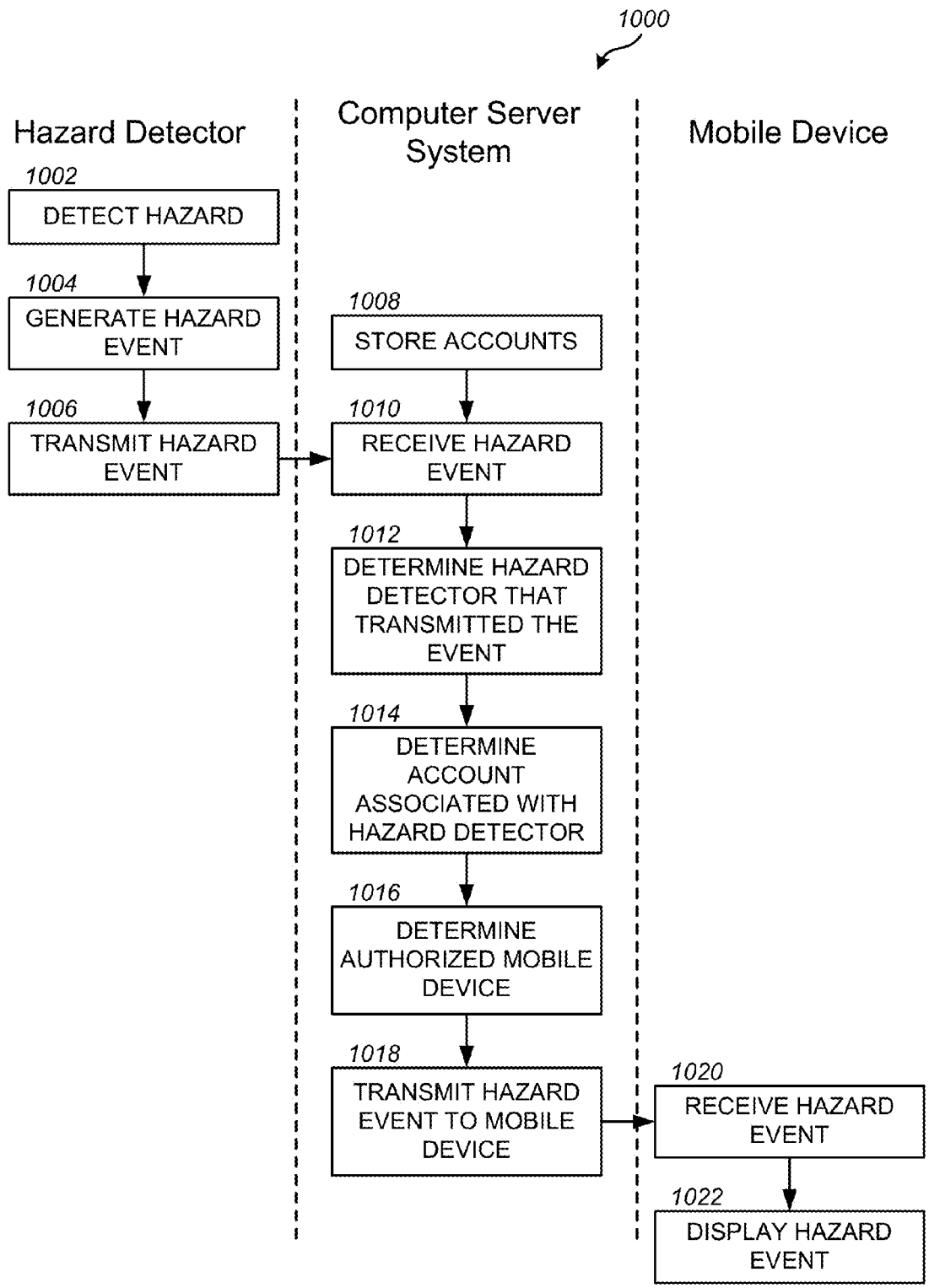
FIG. 10 is an interaction flowchart of one embodiment of a process for displaying hazard events in a user interface on a mobile device remote from the hazard detector.

FIG. 10 is an interaction flowchart of one embodiment of a process 1000 for displaying hazard events in a user interface on a mobile device remote from the hazard detector. The flow chart illustrates the interactions between three components: a hazard detector, a computer server system, and a mobile device. The hazard detector can be a smart hazard detector, such as hazard detector 104 described herein above and illustrated in FIG. 4. The computer server system can include one or more computer servers, such as computer server system 164 described herein above with reference to FIG. 2. The mobile device can be a mobile phone, tablet, or laptop computer of a user. In other embodiments, it can be any computer, such as a desktop computer, instead of a mobile device.

Process 1000 begins at block 1002, when the hazard detector is triggered by the presence of a hazardous substance. In one embodiment, the hazard detector is triggered if the level of hazardous substance present (i.e., the amount or concentration of the hazardous substance) is greater than a threshold setting. In other embodiments, the hazard detector can include multiple threshold settings for detecting different levels of the hazardous substance. At block 1004, the hazard detector generates a hazard event indicating the detection of the hazardous substance. The hazard event can include a unique identification of the hazard detector, as well as other information such as the level of the hazardous substance or data from other sensors in the hazard detector. At block 1006, the hazard detector transmits the hazard event to the computer server system.

With reference now to the computer server system, at block 1008, accounts are stored. In one embodiment, an account is stored when a user registers a hazard detector. In another embodiment, an account is stored when a user creates an account by specifying user information including a username and password. At block 1010, the hazard event is received. The computer server system can determine which hazard detector transmitted the hazard event using the unique identification of the hazard detector that is included in the hazard event (block 1012). In one embodiment, the unique identification is the media access control address (MAC address) of the hazard detector. In other embodiments, the unique identification can be any arbitrarily defined combination of characters and numbers.

At block 1014, the computer server system determines an account that is associated with the hazard detector that transmitted the hazard event. In one embodiment, the account can be determined by doing a search or a query in a database of accounts using the unique identification of the hazard detector. In another embodiment, the stored accounts are indexed by the hazard detectors associated with each account and the account can be determined using a lookup table. At block 1016, the computer server system determines that the mobile device is authorized to access the account. This determination can be made using, for example, a username and password that the user entered when logging into the mobile application or user interface. Thus, in other embodiments, this block can be performed before the hazard event is received at block 1010. At block 1018, the hazard event is transmitted to the mobile device. In some embodiments, additional information can be included with the hazard event before transmission. For example, the computer server system can include a location, e.g., a room name, that is associated with the hazard detector in the hazard event. In another embodiment, the computer server system can include a message in the hazard event that explains the event or provides some other instructions.

At block 1020, the mobile device receives the hazard event. At block 1022, the mobile device displays the hazard event. More specifically, a mobile application displays the hazard event in a user interface according to any of the embodiments described herein. Embodiments for displaying hazard events are described in detail herein below with reference to FIGS. 11-17.

Figure 11:
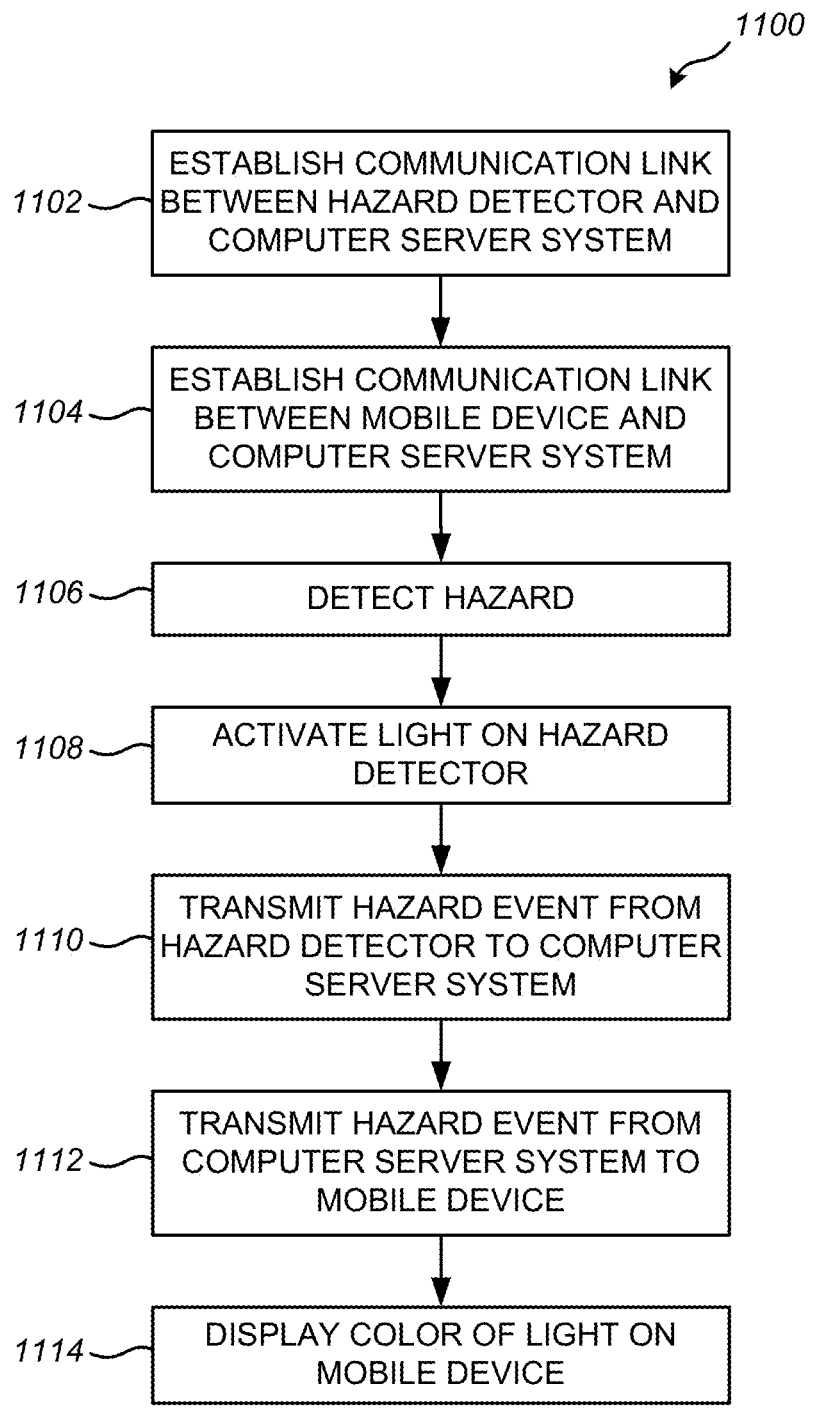
FIG. 11 is a flowchart of another embodiment of a process for displaying hazard events in a user interface on a mobile device remote from the hazard detector.

FIG. 11 is a flowchart of another embodiment of a process 1100 for displaying hazard events in a user interface on a mobile device remote from the hazard detector. Process 1100 starts at block 1102, wherein a communication link is established between a hazard detector and the computer server system. In one embodiment, this communication link includes a wireless segment, e.g., between the hazard detector and a wireless router in the home that connects the hazard detector to the internet and the computer server system. At block 1104, a second communication link is established between a mobile device and the computer server system. The second link also includes a wireless segment. In some embodiments, the user interface is a web page and the hazard events can be displayed at any computing device, in which case a wireless segment is not included.

At block 1106, the hazard detector detects a hazardous substance such as smoke or CO. In one embodiment, the hazardous substance is detected when the level of the hazardous substance present at the hazard detector is greater than a preset threshold. The threshold defines a level of hazardous substance at which an alarm or pre-alarm event should be generated. In some embodiments, multiple thresholds can be used by the hazard detector, some corresponding to levels at which pre-alarms should be generated and some corresponding to levels at which an alarm should be generated. Different thresholds can be used for different hazardous substances. Some threshold settings can also be used to generate notifications indicating that the hazardous situation is improving. For example, if the level of hazardous substance decreases below a threshold setting, an event can be generated that informs the user that the hazardous substance is clearing out.

At block 1108, a light is activated on the hazard detector to indicate the detection of the hazardous substance. In one embodiment, this light includes the LED lights described herein above with reference to FIG. 5, and any of the visual effects described with reference to FIGS. 6-9 can be generated by the light. In one embodiment, a yellow light indicates a pre-alarm level of hazardous substance has been detected and a red light indicates an alarm or emergency level of hazardous substance has been detected. A green light can be used for notifications not associated with the detection of a hazardous substance, such as to indicate that the battery level is good or all sensors are functioning properly.

At block 1110, a hazard event is transmitted from the hazard detector to the computer server system. After the computer server system processes the hazard event, the hazard event is transmitted to the mobile device at block 1112. A native mobile application or a web browser on the mobile device displays the hazard event by displaying the same color as the light on the triggered hazard detector. In some embodiments, the user interface also displays color in the same shape as the light on the hazard detector (e.g., a ring) and/or generates the same visual effects as the light on the hazard detector.

Figure 12:
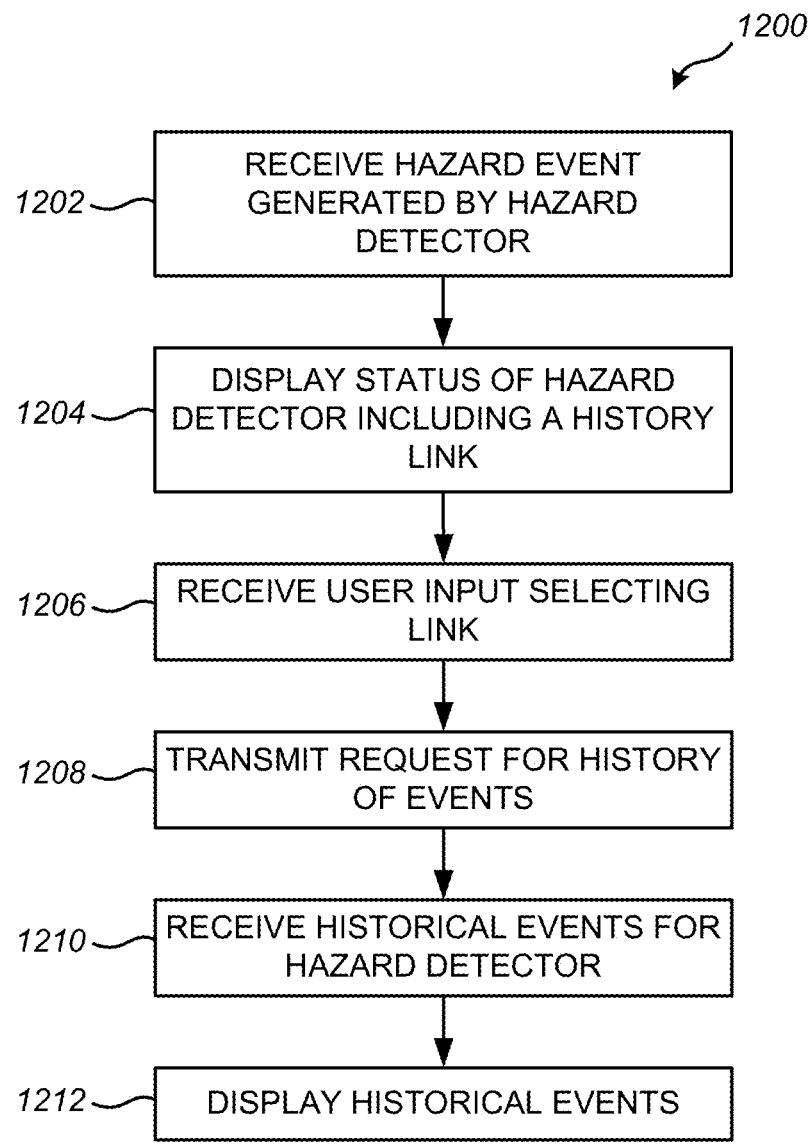
FIG. 12 is a flowchart of a further embodiment of a process for displaying hazard events in a user interface on a mobile device remote from the hazard detector.

FIG. 12 is a flowchart of a further embodiment of a process 1200 for displaying hazard events in a user interface on a mobile device remote from the hazard detector. At block 1202, a hazard event that is generated by the hazard detector is received. In one embodiment, the hazard event is received by an application such as a mobile application or web application. At block 1204, the status of the hazard detector is displayed including a link for a history of the hazard detector. In other embodiments, the link can be for a history of all hazard detectors associated with the same account. The link can be a button or hyperlink that can be selected or pressed by a user in a user interface.

After receiving user input selecting the link at block 1206, a request is transmitted for a history of events at block 1208. The request can be transmitted to the computer server system and can include an identifier for the hazard detector or other information. At block 1210, historical events are received for the hazard detector as a response to the request. At block 1212, the historical events are displayed according to any of the embodiments described herein. Detailed descriptions of embodiments for displaying historical events will be described herein below with reference to FIG. 17.

Figure 13:
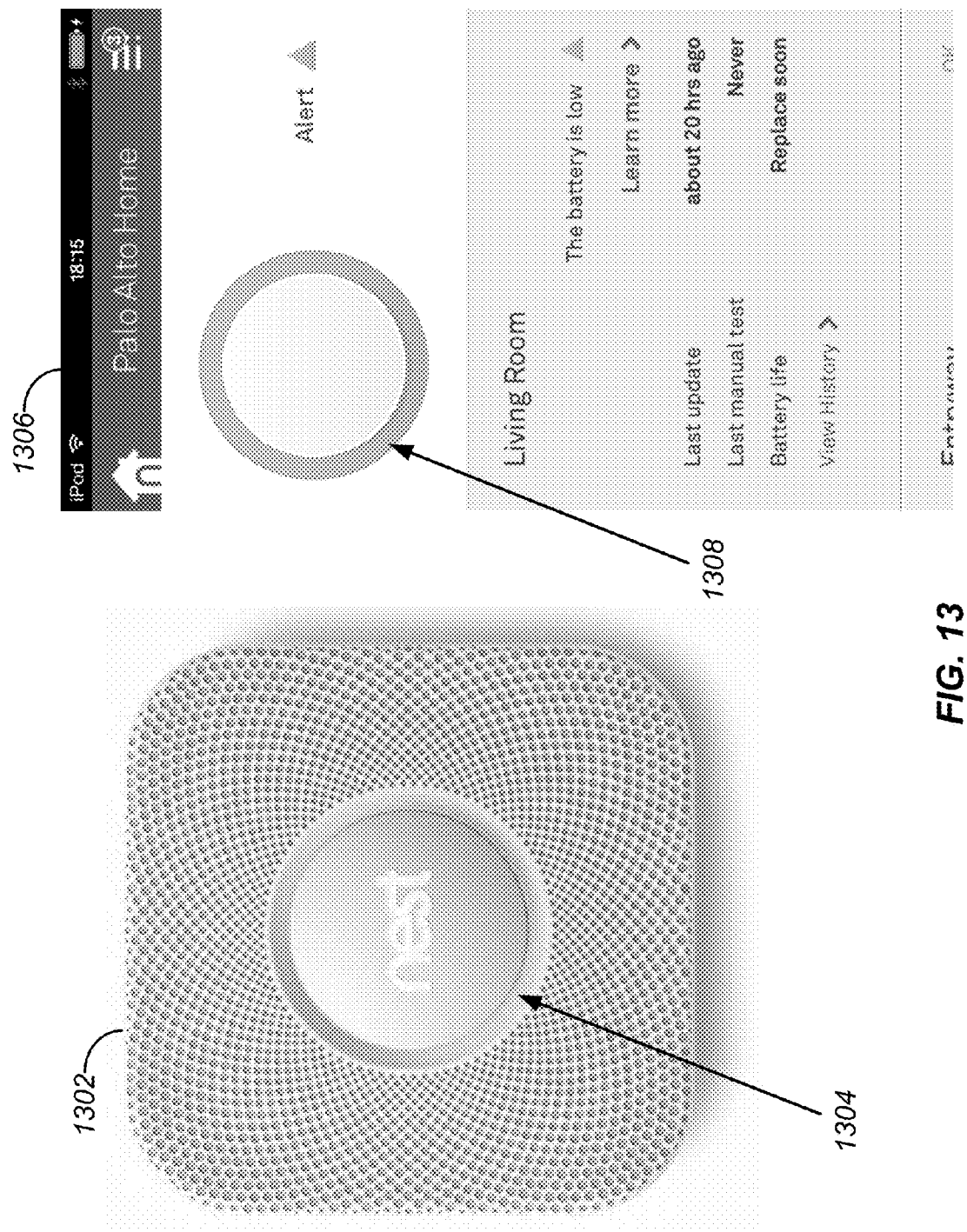
FIG. 13 is an illustration of a hazard detector and a user interface on a mobile device showing matching colors, according to an embodiment.

FIG. 13 is an illustration of a hazard detector 1302 and a user interface 1306 on a mobile device showing matching colors, according to an embodiment. In this illustration, hazard detector 1302 has activated a light 1304 with a yellow color and in the shape of a ring. User interface 1306 displays a ring 1308 that also has a yellow color. In this embodiment, the yellow color is used to indicate that the battery level of the hazard detector 1302 is low. User interface 1306 can display the yellow colored ring 1308 after receiving a battery event generated by hazard detector 1302 indicating the low battery level. By displaying the color or shape on the user interface 1306 that is the same as the light on the hazard detector 1302, the user is presented with a consistent indicator for messages generated by the hazard detector 1302.

Figure 14:
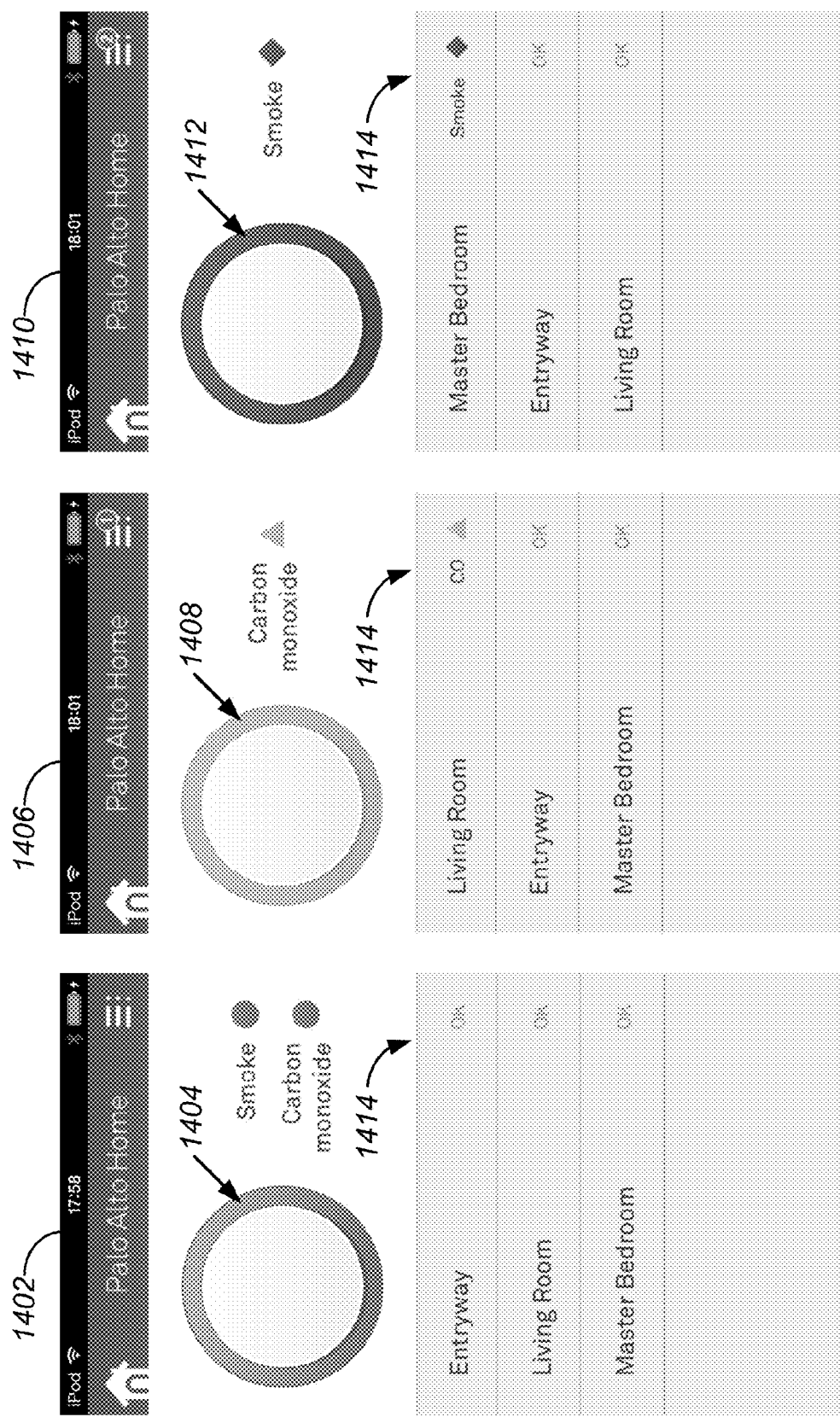
FIG. 14 is an illustration of a user interface on a mobile device displaying statuses for multiple hazard detectors, according to an embodiment.

FIG. 14 is an illustration of a user interface on a mobile device displaying statuses for multiple hazard detectors, according to an embodiment. The user interface is logged in to an account that includes three different hazard detectors: Entryway, Living Room, and Master Bedroom. A status for each hazard detector is displayed in list 1414. In one embodiment, the list 1414 is a dynamic list in which the hazard detectors are ordered according to the severity or urgency of the status of each hazard detector. Thus, when a hazard detector reports a hazard event, the list is automatically rearranged and the hazard detector that is reporting the most severe event is displayed at the top of the list 1414. In another embodiment, if a hazard detector associated with the account is not connected to the computer server system, a status is not displayed for the hazard detector. If the mobile device is not connected to the computer server system, then a status is not displayed for any hazard detectors. This ensures that the user does not receive outdated or misleading information regarding the status of a hazard detector.

Three different states of the user interface are depicted in this illustration. At state 1402, the user interface displays a green colored ring 1404 to indicate that all of the hazard detectors are not detecting any hazardous substances. It can also indicate that all three hazard detectors are functioning properly and their battery levels are not low. At state 1406, the Living Room hazard detector has detected a pre-alarm level of CO. The Living Room hazard detector is moved to the top of the list 1414 and a yellow colored ring 1408 is displayed indicating the pre-alarm level of CO detected. At state 1410, the Living Room hazard detector no longer detects CO, but the Master Bedroom hazard detector has detected an emergency level of smoke. The status for the Master Bedroom hazard detector is now displayed at the top of the list 1414 and a red colored ring 1412 is displayed indicating the emergency level of smoke detected. If multiple hazard detectors associated with the account have detected a hazardous substance, the ring that is displayed above list 1414 can be in a color that matches the most severe event.

Figure 15:
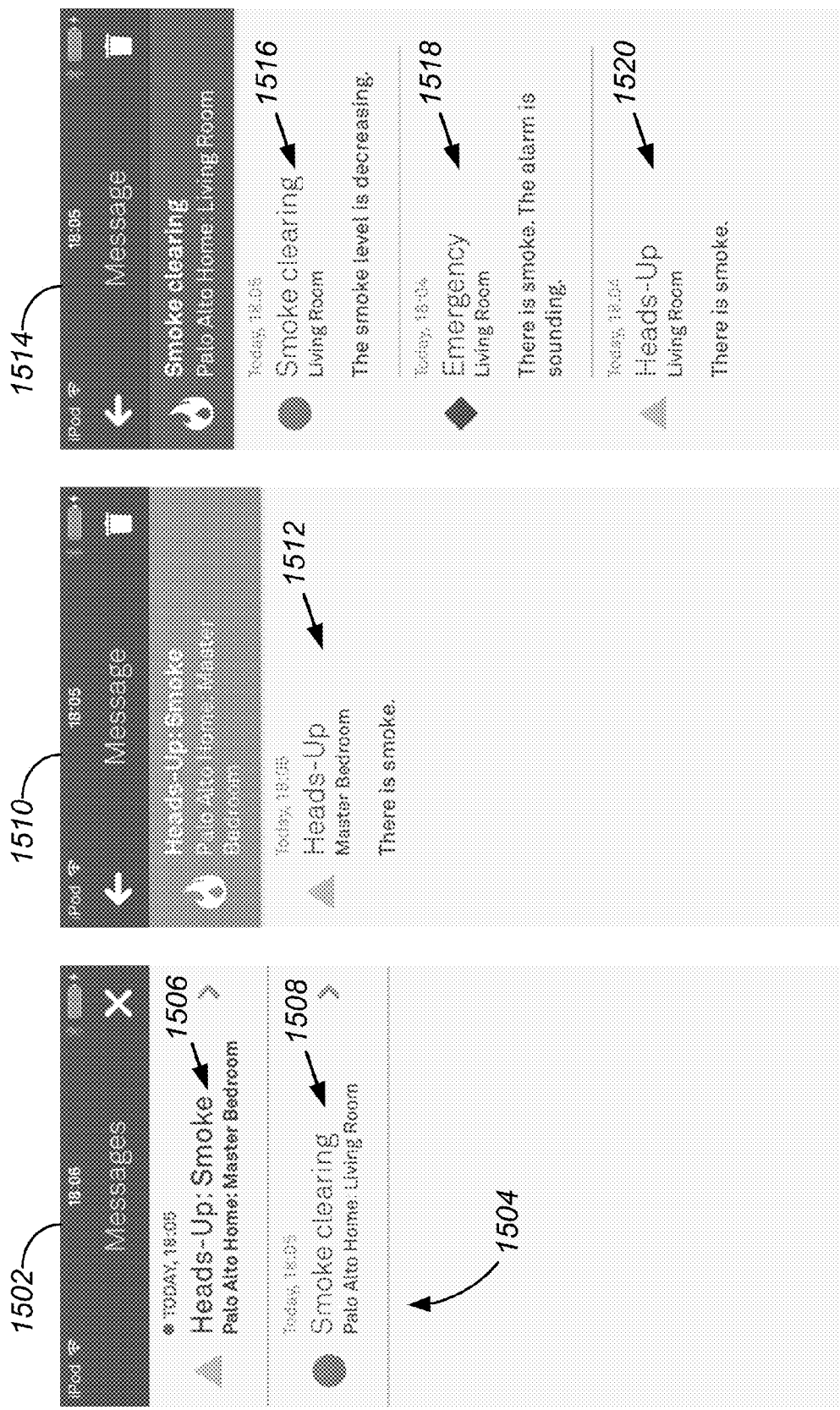
FIG. 15 is an illustration of a user interface on a mobile device displaying messages for events generated by hazard detectors, according to an embodiment.

FIG. 15 is an illustration of a user interface on a mobile device displaying messages for events generated by hazard detectors, according to an embodiment. At state 1502, the user interface is displaying a list of message threads 1504, which are groups of messages for hazard events that are related. For example, during a hazardous situation, more than one hazard detectors can be triggered by the presence of a hazardous substance. In one embodiment, the hazard detectors report different levels of events, such as a pre-alarm level and emergency level. Hazard detectors can also report a cleared event when the level of hazardous substance drops below a preset threshold, or if the hazard detector no longer detects the hazardous substance. Furthermore, hazard detectors can be triggered for different hazardous substances during a hazardous situation, e.g., smoke and CO. All of the messages for events that occur during a hazardous situation can be grouped into a single thread to organize the messages.

In one embodiment, a new thread is created when a hazard detector reports a hazard event (e.g., pre-alarm or emergency for smoke or CO) and no other hazard detector associated with the same account is reporting a hazard event. After a new thread is created, any subsequent hazard events reported by hazard detectors associated with the same account are grouped into the thread. Once all hazard detectors associated with the account report a cleared event for each hazardous substance that was detected, the thread is closed and a new thread is started for the next hazard event reported. This process can be performed by the computer server system or the mobile application. In one embodiment, the computer server system associates a tag with each hazard event received from a hazard detector and transmits the tag along with the hazard event to the mobile device. The tag indicates whether the hazard event should be placed into an existing thread or a new thread.

In one embodiment, user interface displays the last event or message received for each thread in the list of message threads 1504. In this illustration, the user interface is displaying two message threads 1506 and 1508. The thread 1506 that is still active can be emphasized by, for example, using a bold font or an indicator to grab the user's attention.

When a user selects a thread, all of the messages in that thread are displayed. At state 1510, the user interface is displaying the messages for thread 1506, which only contains one message for a pre-alarm hazard event 1512 in this embodiment. At state 1514, the user interface is displaying the messages for thread 1508, which contains three messages for a cleared event 1516, an emergency hazard event 1518, and a pre-alarm hazard event 1520. The messages can be displayed in chronological order or reverse chronological order.

Figure 16:
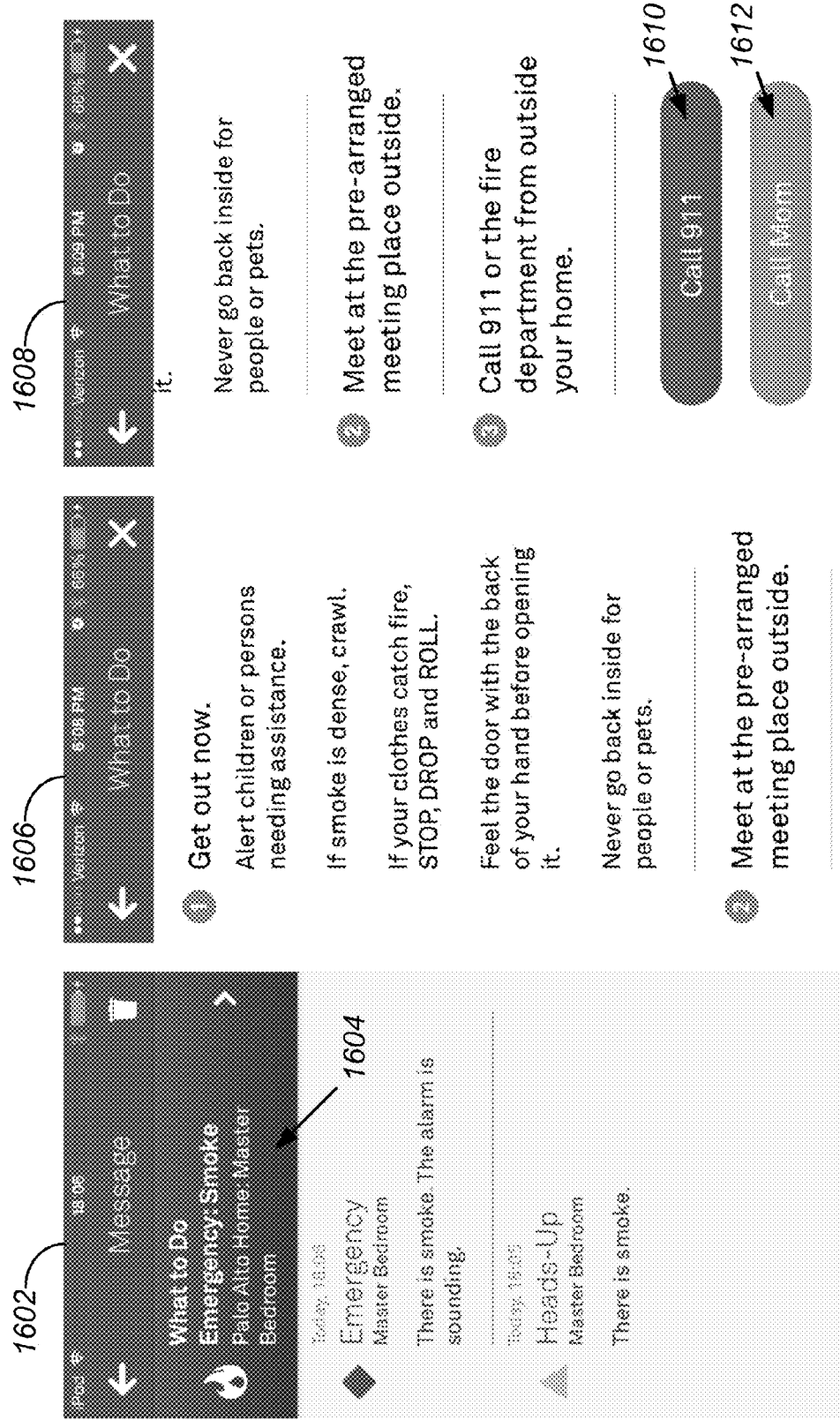
FIG. 16 is an illustration of a user interface on a mobile device displaying a what to do message for an emergency situation, according to an embodiment.

FIG. 16 is an illustration of a user interface on a mobile device displaying a what to do message for an emergency situation, according to an embodiment. In this embodiment, the what to do message is displayed if the last event reported for the account is an emergency hazard event. At state 1602, the what to do message 1604 is displayed at the top of a message thread. At state 1606, instructions are displayed for recommended actions to take during an emergency situation. In one embodiment, the instructions are displayed in response to a user's selection of the what to do message 1604.

At state 1608, two links 1610 and 1612 are displayed, which can be hyperlinks or buttons. In one embodiment, when a user selects link 1610, logic embedded in the link causes the dialer interface of the mobile device to be displayed and inserts a universal emergency number, such as 911, into the dialer interface. Thus, the user only needs to press the call button to make an emergency call. In another embodiment, selecting link 1610 will cause the mobile device to dial the universal emergency number. If link 1612 is selected, embedded logic can cause the mobile device to display the dialer interface with a user defined emergency contact number inserted, or dial the user defined emergency contact number. The emergency contact can be predefined by the user by selecting a contact from the list contacts stored on the phone or in a cloud account.

Figure 17:
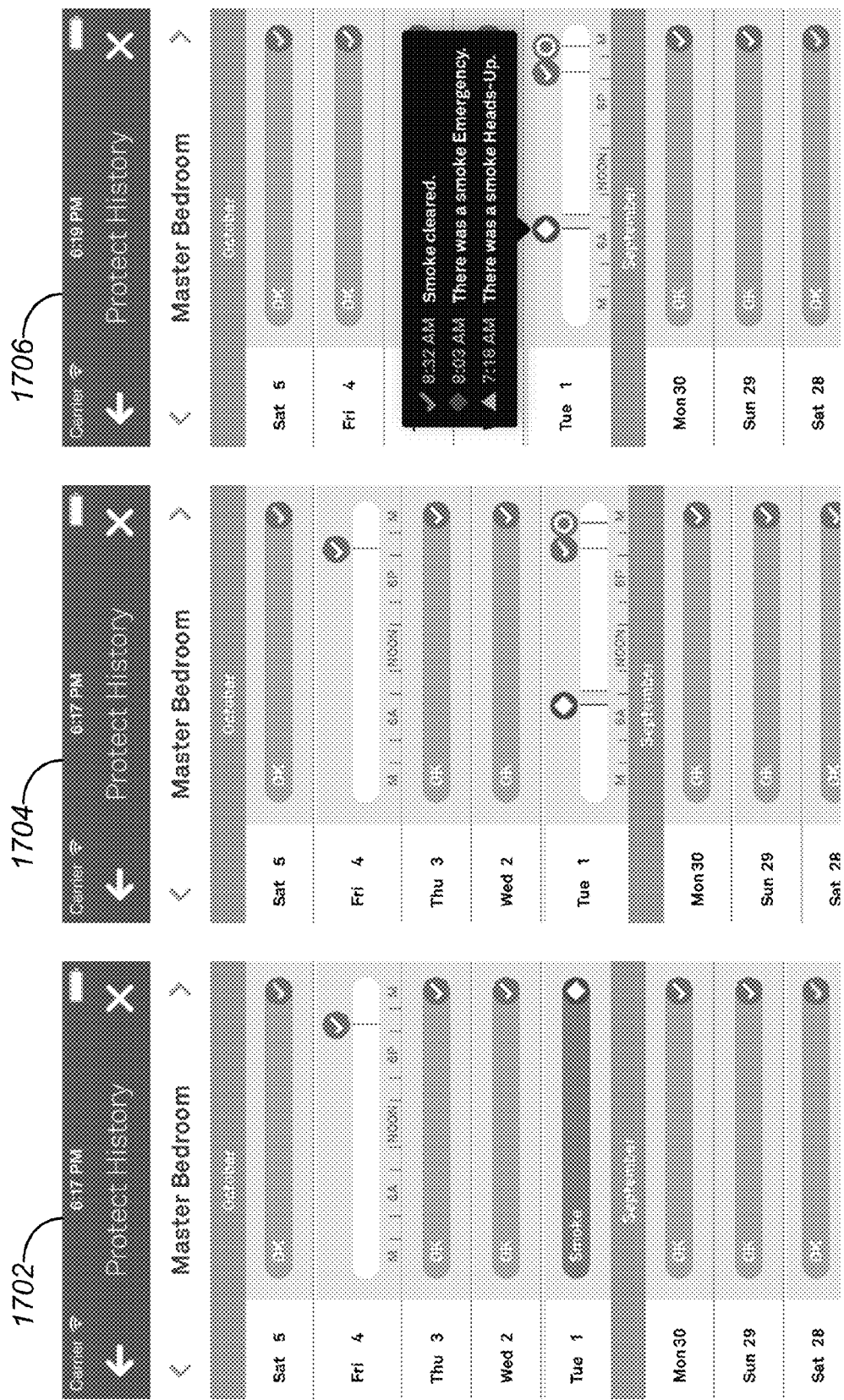
FIG. 17 is an illustration of a user interface on a mobile device displaying a history of events for a hazard detector, according to an embodiment.

FIG. 17 is an illustration of a user interface on a mobile device displaying a history of events for a hazard detector, according to an embodiment. In this embodiment, the history of events is specific to one hazard detector. The history is displayed when a user selects a link, which can be included as part of the status for each hazard detector (see FIG. 13, user interface 1306, for an illustration of an example history link). In other embodiments, the history of events can be thread specific or account specific.

At state 1702, the user interface displays a list of dates for which the hazard detector generated events. In one embodiment, the hazard detector generates at least one check-in event each day, to indicate whether the hazard detector is functioning properly and the status of the battery level. There can be a maximum number of dates that the user interface displays historical events for. In this embodiment, the user interface displays historical events for eight dates. A summary is displayed for each date in the list. In one embodiment, the summary indicates the most severe historical event generated by the hazard detector on each date. In another embodiment, the summary indicates the last historical event generated by the hazard detector on each date.

When a user selects a specific date, a timeline is displayed in place of the summary for that date. At state 1704, the user interface is displaying a timeline for Tuesday, October $1^{st}$. The historical events that were generated by the hazard detector on that date are plotted as markers on the timeline, at positions corresponding to the time that each historical event was generated. A symbol or indicator is displayed above the marker that indicates the type of event. In one embodiment, a thread of historical events is also indicated on the timeline by a shaded region corresponding to the duration of the thread.

At state 1706, the user interface is displaying a tooltip for a thread. The tooltip can be displayed when a user selects a marker or shaded region on the timeline. The tooltip provides details for the event or thread corresponding to the selection. In this embodiment, the tooltip is displaying the descriptions for three events that were generated as part of a thread.

Figure 18:
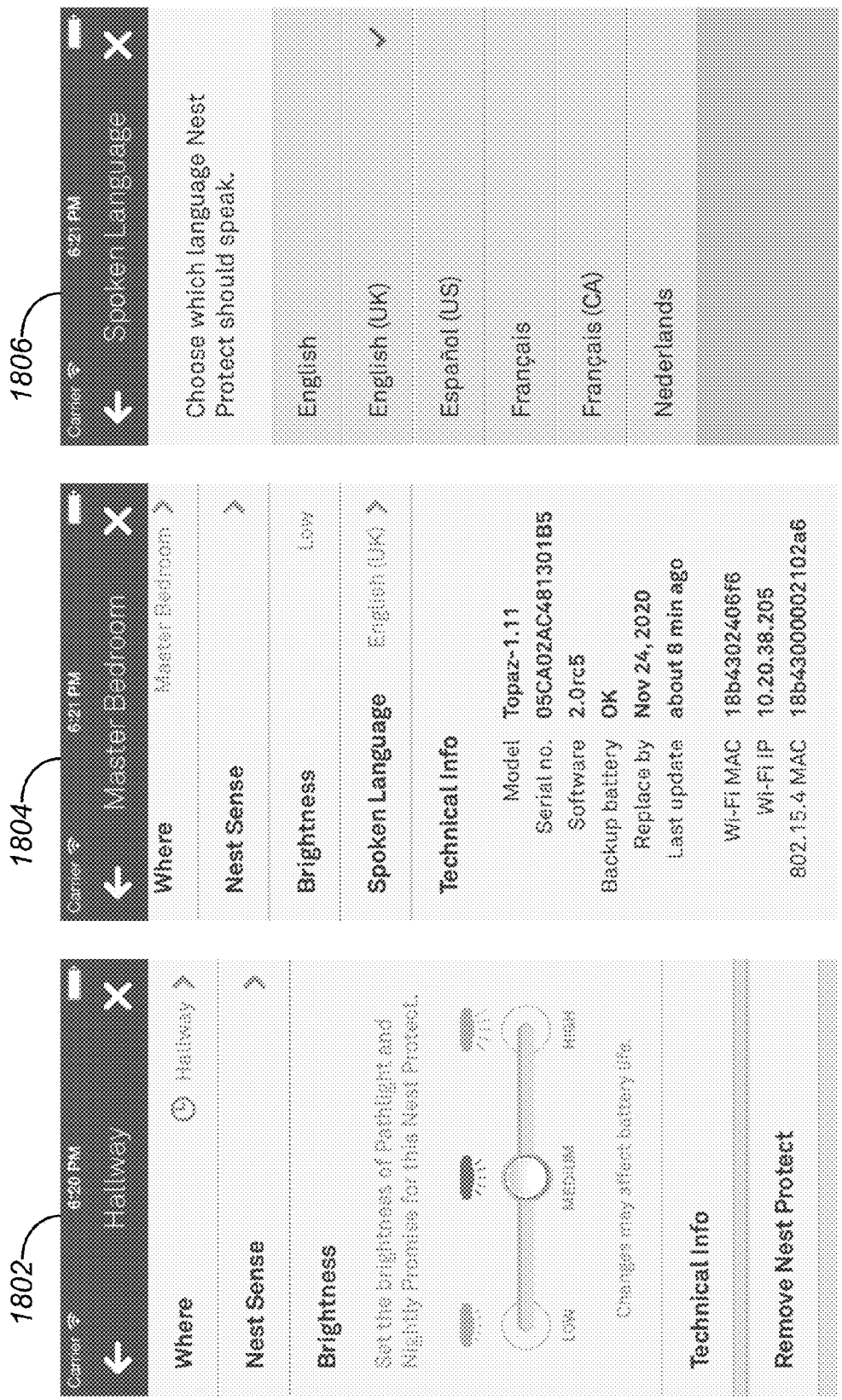
FIG. 18 is an illustration of a user interface on a mobile device displaying adjustable settings for a hazard detector, according to an embodiment.

FIG. 18 is an illustration of a user interface on a mobile device displaying adjustable settings for a hazard detector, according to an embodiment. In this embodiment, multiple settings and groups of settings are displayed in a list in the user interface. The list also displays the current value that is in effect for each setting on the right side of the list.

At state 1802, the user interface is displaying an expanded area for the Brightness setting in response to a user selecting the Brightness setting by, for example, touching the Brightness setting on a touch screen or clicking on the Brightness setting with a mouse. A switch is displayed in the expanded area that allows the user to adjust the setting. A description for the setting is also displayed in the expanded area. The Brightness Setting allows the user to adjust the brightness of a light source that is included in the hazard detector, which can be used as a night light or to communicate messages to the user.

When a user selects a different setting, such as the Technical Info setting, the display area for the Brightness is reduced. Since the display area of the mobile device is limited, this allows the user interface to display more information without having to display a different screen, which can be confusing to a user. At state 1804, the user interface is displaying a reduced Brightness setting area and an expanded Technical Info setting area. The Technical Info setting displays technical details for the hazard detector, including model, serial number, software version, battery status, replace by date of when the hazard detector should be replaced, last update time, MAC addresses, and internet protocol (IP) address.

The arrow on the right side of the list indicates that a new screen will be displayed for the setting or group of settings. At state 1806, the user interface is displaying the screen for the Spoken Language setting, which allows the user to adjust the language that is spoken by the hazard detector.

Figure 19:
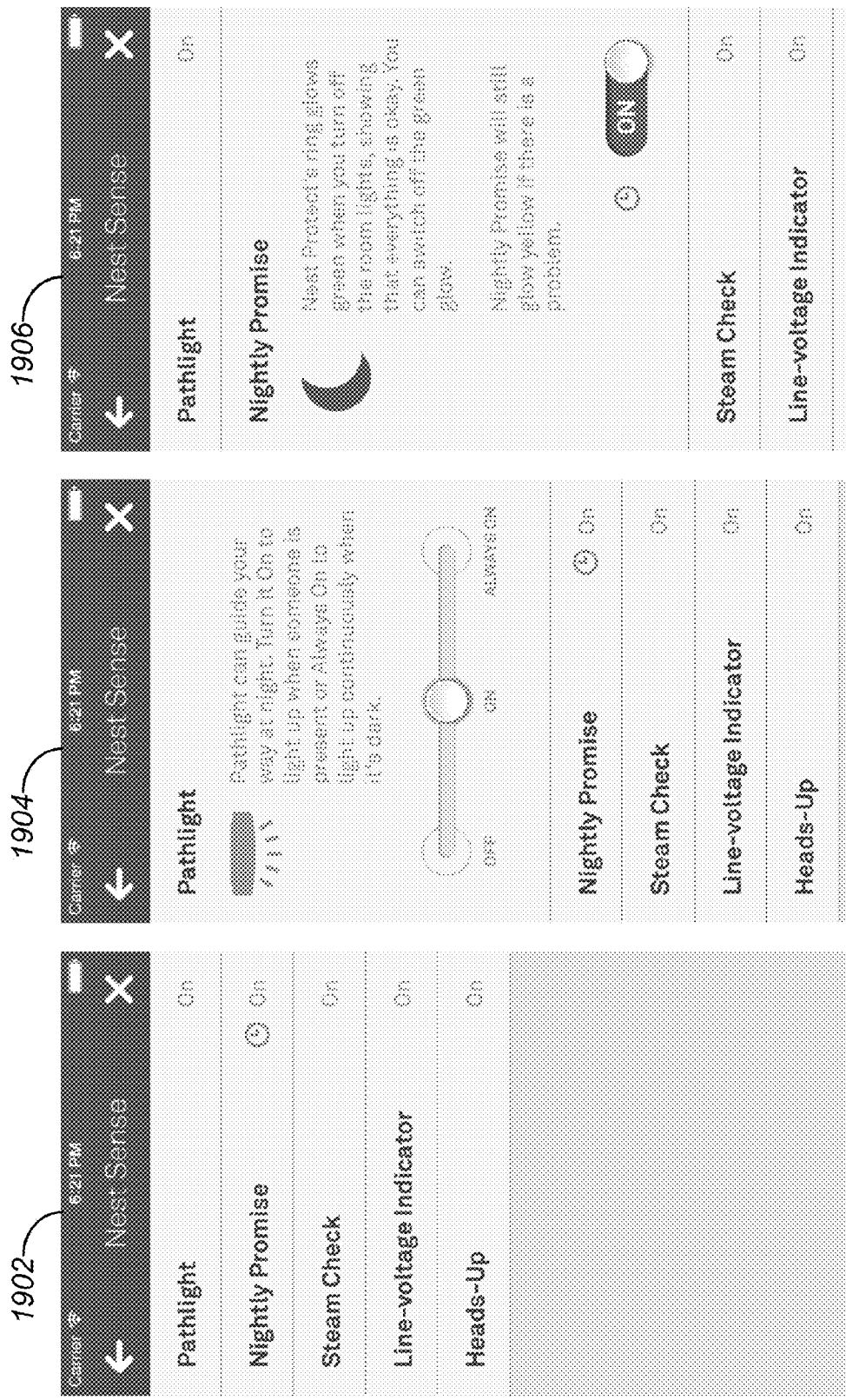
FIG. 19 is an illustration of a user interface on a mobile device displaying additional adjustable settings for a hazard detector, according to an embodiment.

FIG. 19 is an illustration of a user interface on a mobile device displaying additional adjustable settings for a hazard detector, according to an embodiment. At state 1902, the Nest Sense group of settings is displayed in the user interface. At state 1904, the user interface is displaying an expanded area for the Pathlight setting. This setting lets the user adjust whether the light source in the hazard detector is activated when it is dark and there is motion, or whether the light source is always activated when it is dark.

At state 1906, the user interface is displaying an expanded area for the Nightly Promise setting. Nightly Promise is a feature that uses the light source to communicate to the user that the hazard detector is functioning properly and the battery level is good by generating a green glow with the light source when the lights are turned off (i.e., when an ambient light sensor in the hazard detector senses a drop in ambient light level).

The clock symbol next to the switch indicates that the user adjusted the setting, but the new value has not been applied yet to the hazard detector and therefore is not in effect. To conserve battery, the hazard detector only communicates with the computer server system at regular intervals unless a hazardous substance is detected. In one embodiment, the hazard detector transmits a check-in event to the computer server system every 24 hours, and adjusted settings are only applied when the hazard detector checks in. Thus, after the user makes the adjustment, the new value of the setting is stored at the computer server system until a check-in event is received from the hazard detector, at which time the new value for the setting is applied.

Figure 20:
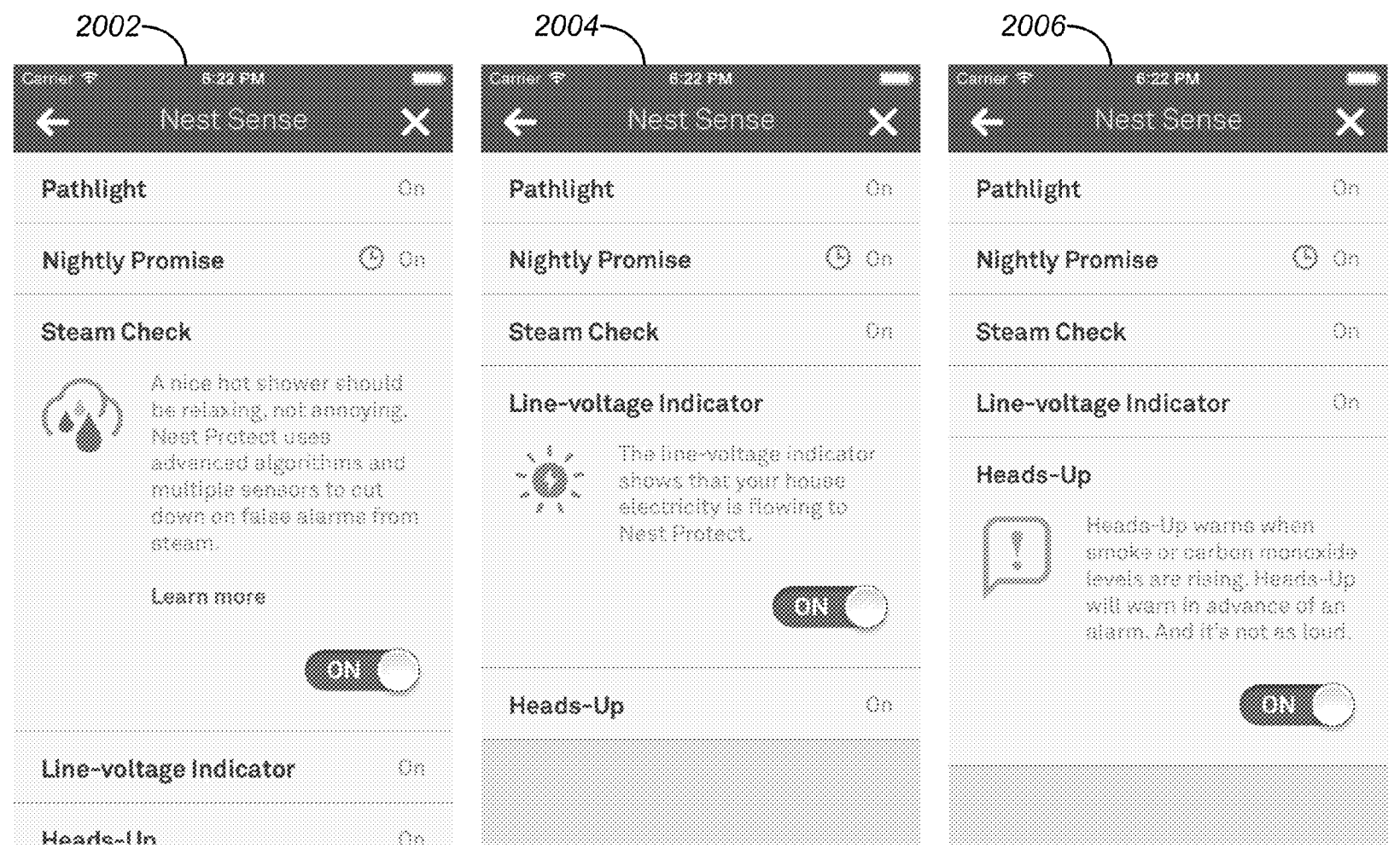

FIG. 20 is an illustration of a user interface on a mobile device displaying further adjustable settings for a hazard detector, according to an embodiment. At state 2002, an expanded area is displayed for the Steam Check setting. When this setting is turned on, the hazard detector uses a humidity sensor to detect steam. In some embodiments, a heat sensor is also used to detect steam. If steam is detected, for example, by detecting an increase in humidity, the hazard detector adjusts one or more thresholds for smoke. By increasing the smoke thresholds at which alerts or alarms are activated, the hazard detector reduces the number of false alarms caused by steam.

At state 2004, the user interface is displaying an expanded area for the Line-voltage Indicator setting. This setting determines whether an indicator, such as an LED light, is activated to indicate that the primary power source of the hazard detector is supplying power. In one embodiment, this setting is only available if the hazard detector is a wired hazard detector, such that the primary power source is the electricity power line of the house. In another embodiment, the indicator can be activated to indicate that the primary power supply is not supplying power.

At state 2006, the Heads-Up setting is expanded in the display area of the user interface. When this setting is activated, the hazard detector provides a pre-alarm when the level of hazardous substance is rising but has not reached an emergency level. Thus, when the detected level of hazardous substance is above a pre-alarm threshold but below an alarm threshold, the hazard detector generates the pre-alarm. The pre-alarm can be in the form of an audible alert or visual alert. In one embodiment, the hazard detector generates audible speech that announces the rising level of hazardous substance and activates a yellow light.

Figure 21:
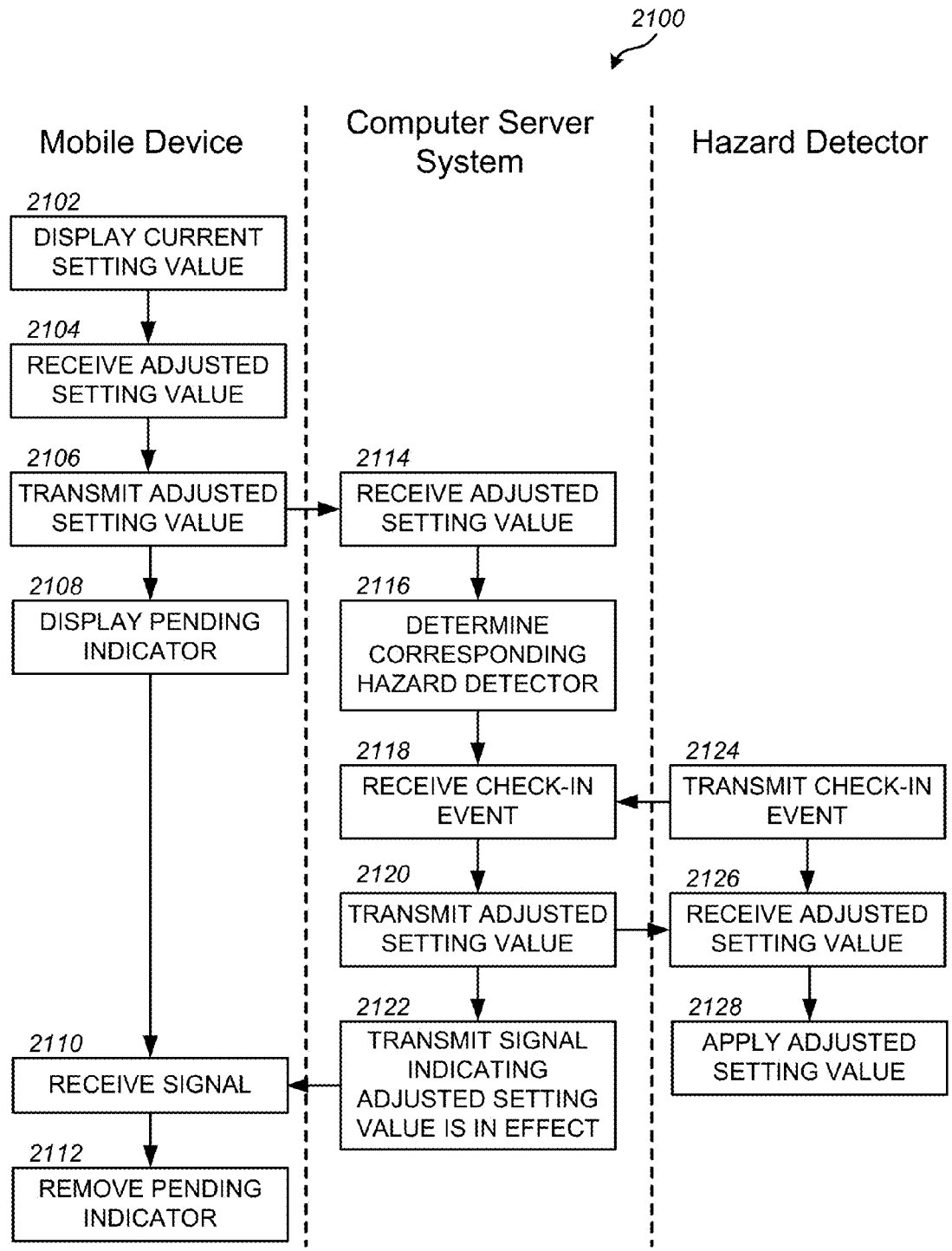
FIG. 21 is an interaction flowchart of one embodiment of a process for adjusting a setting of a hazard detector on a mobile device remote from the hazard detector.

FIG. 21 is an interaction flowchart of one embodiment of a process 2100 for adjusting a setting of a hazard detector on a mobile device remote from the hazard detector. The flow chart illustrates the interactions between three components: a mobile device, a computer server system, and a hazard detector.

At block 2102, the mobile device displays a current value for the setting in a user interface. The current value for the setting is the value that is in effect on the hazard detector. At block 2104, the user interface receives input from a user that adjusts the setting to an adjusted value. At block 2106, the adjusted value is transmitted to the computer server system, and at block 2108, a pending indicator is displayed for the setting in the user interface. The pending indicator tells the user that the adjusted value for the setting has not been applied yet. After the user interface receives a signal from the computer server system indicating that the adjusted value for the setting has been applied (block 2110), the pending indicator is removed from the display of the setting (block 2112).

With reference now to the computer server system, at block 2114, the adjusted value for the setting is received. At block 2116, the computer server system determines which hazard detector the adjusted setting value corresponds to. In one embodiment, the user interface transmits a unique identifier of the hazard detector with the adjusted setting value, and the computer server system can extract the identifier to determine the corresponding hazard detector.

The computer server system then waits for a check-in event from the hazard detector. At block 2118, the check-in event is received from the hazard detector, and at block 2120, the computer system transmits the adjusted value to the hazard detector so that it can be applied to the setting. In one embodiment, the computer server system performs a conflict resolution process before transmitting the adjusted value at block 2120. The computer server system can receive multiple adjustments to the setting before a check-in event is received. For example, two different users of the hazard detector can both make adjustments to the setting from their own mobile device, or one adjustment can be made from the hazard detector and another adjustment can be made from a mobile device. The resolution process determines which adjusted value to apply to the setting. In one embodiment, the determination is made based on the time that each adjustment was made. Thus, if the computer server system received multiple adjustments to the setting before the hazard detector checked in, the most recent adjustment will be transmitted to the hazard detector at block 2120.

At block 2122, the computer server system transmits the signal to the mobile device indicating the adjusted value is in effect. In this embodiment, the computer server system assumes that the adjusted value will be applied and take effect if it was successfully transmitted to the hazard detector. In other embodiments, the computer server system waits for a confirmation from the hazard detector indicating that the adjustment has been applied before transmitting the signal to the mobile device at block 2122.

At block 2124, the hazard detector transmits the check-in event to the computer server system. In this embodiment, the hazard detector checks in at regular time intervals and setting adjustments are only applied during check-in. Thus, if a hazardous substance is detected and a hazard event is transmitted, the computer server system would not transmit the adjusted setting value to the hazard detector in response to receiving the hazard event. This reduces traffic on the communication channels during a hazardous situation, which helps ensure that emergency communication transmissions will be successful. At block 2126, the hazard detector receives the adjusted value for the setting, and at block 2128, the adjusted value is applied to the setting according to any of the embodiments described herein.

Figure 22:
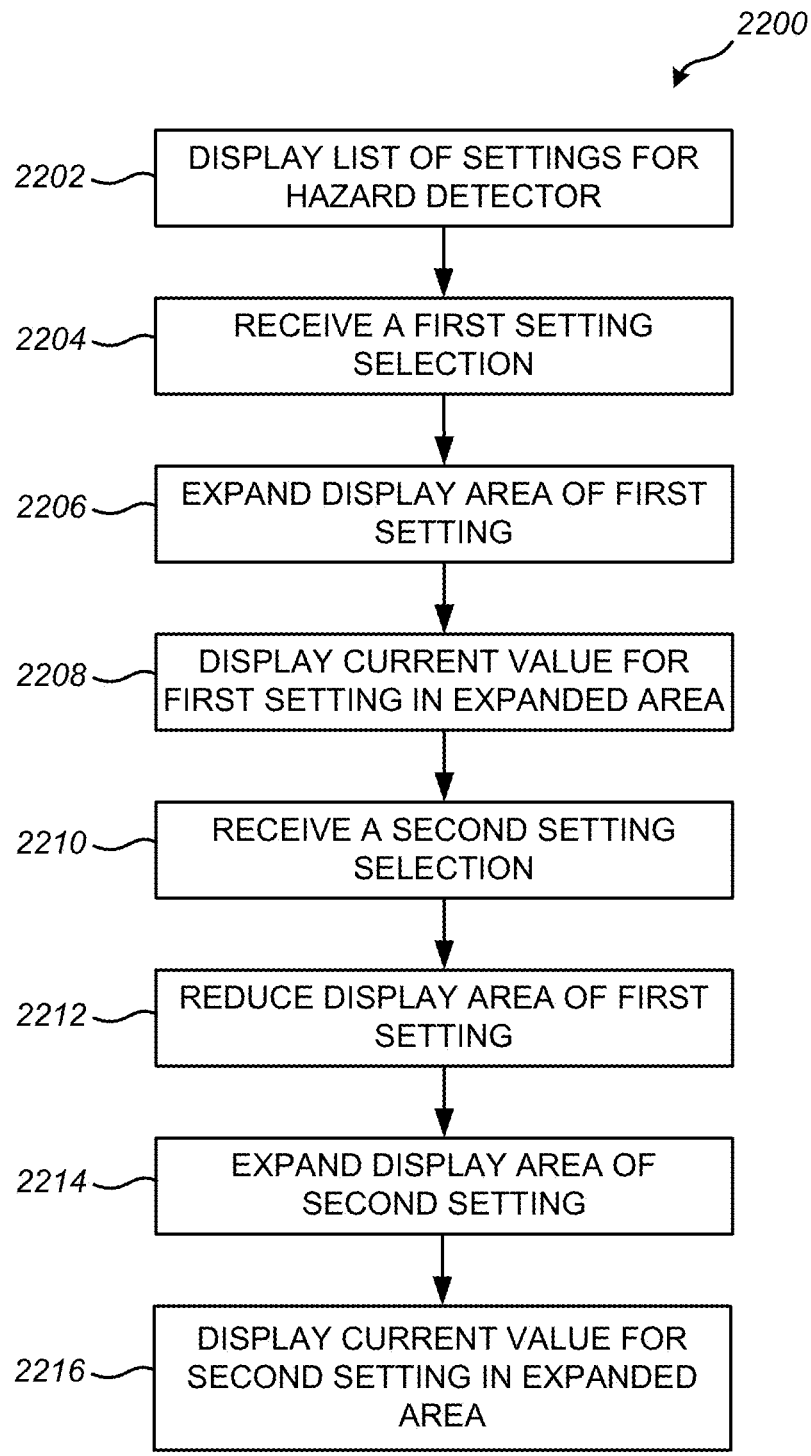
FIG. 22 is a flowchart of another embodiment of a process for adjusting a setting of a hazard detector on a mobile device remote from the hazard detector.

FIG. 22 is a flowchart of another embodiment of a process 2200 for adjusting a setting of a hazard detector on a mobile device remote from the hazard detector. In this embodiment, process 2200 is performed by a native application including a user interface executed on the mobile device. In other embodiments, process 2200 can be performed by any application or user interface, such as a web application.

At block 2202, the user interface displays a list of settings for the hazard detector. In this embodiment, the list of settings includes at least two expandable settings. The list can also include groups of settings or settings that display a new screen when selected. At block 2204, user input is received selecting a first setting. In response to the user input, the display area for the first setting is expanded at block 2206. A current value for the first setting is displayed in the expanded area at block 2208. A switch or button can also be displayed in the expanded area to allow the user to adjust the setting. In one embodiment, the current value is displayed by the position of the switch or button.

At block 2210, a second user input is received selecting a second setting from the list. The display area of the first setting is reduced back to the original size at block 2212 in response to the second user input, and at block 2214, the display area of the second setting is expanded. The current value for the second setting is also displayed in the expanded area at block 2216. In this way, a convenient user interface is provided to the user for adjusting multiple settings of the hazard detector on the mobile device.

Figure 23:
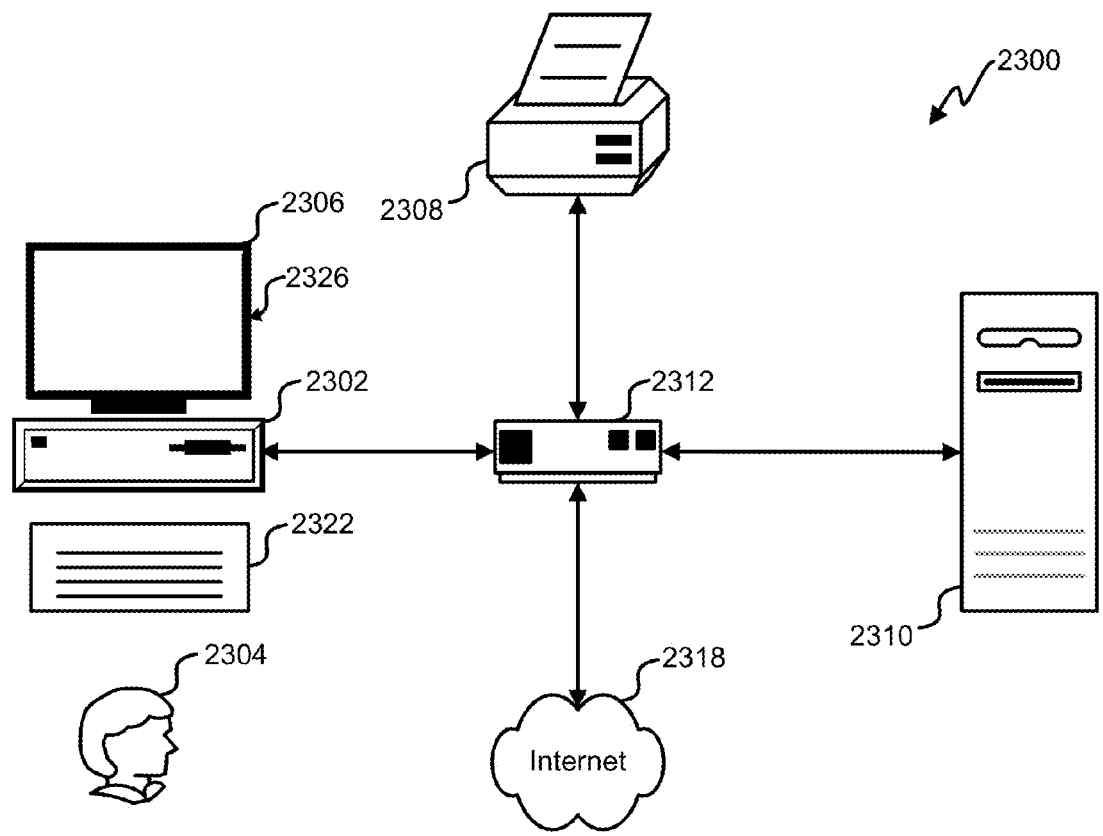
FIG. 23 is a block diagram of an exemplary environment for implementing one embodiment of a system for generating a user interface on a mobile device remote from a hazard detector.

FIG. 23 is a block diagram of an exemplary environment for implementing one embodiment of a system for generating a user interface on a mobile device remote from a hazard detector. The exemplary environment includes a computer system 2300 that can be used by a user 2304 to remotely control, for example, one or more of the smart devices according to one or more of the embodiments described herein. The computer system 2300 can alternatively be used for carrying out one or more of the server-based processing described herein above or as a processing device in a larger distributed computer server system for carrying out processing. The computer system 2300 can include a computer 2302, keyboard 2322, a network router 2312, a printer 2308, and a monitor 2306. The monitor 2306, processor 2302 and keyboard 2322 are part of a computer system 2326, which can be a laptop computer, desktop computer, handheld computer, mainframe computer, etc. The monitor 2306 can be a CRT, flat screen, etc.

A user 2304 can input commands into the computer 2302 using various input devices, such as a mouse, keyboard 2322, track ball, touch screen, etc. If the computer system 2300 comprises a mainframe, a designer 2304 can access the computer 2302 using, for example, a terminal or terminal interface. Additionally, the computer system 2326 may be connected to a printer 2308 and a server 2310 using a network router 2312, which may connect to the Internet 2318 or a WAN. While only one server 2310 is shown in the figure, it is understood that computer system 2326 can be connected to any number of servers.

The server 2310 may be used to store additional software programs and data. In one embodiment, software implementing the systems and methods described herein can be stored on a storage medium in the server 2310. Thus, the software can be run from the storage medium in the server 2310. In another embodiment, software implementing the systems and methods described herein can be stored on a storage medium in the computer 2302. Thus, the software can be run from the storage medium in the computer system 2326. Therefore, in this embodiment, the software can be used whether or not computer 2302 is connected to network router 2312. Printer 2308 may be connected directly to computer 2302, in which case, the computer system 2326 can print whether or not it is connected to network router 2312.

Figure 24:
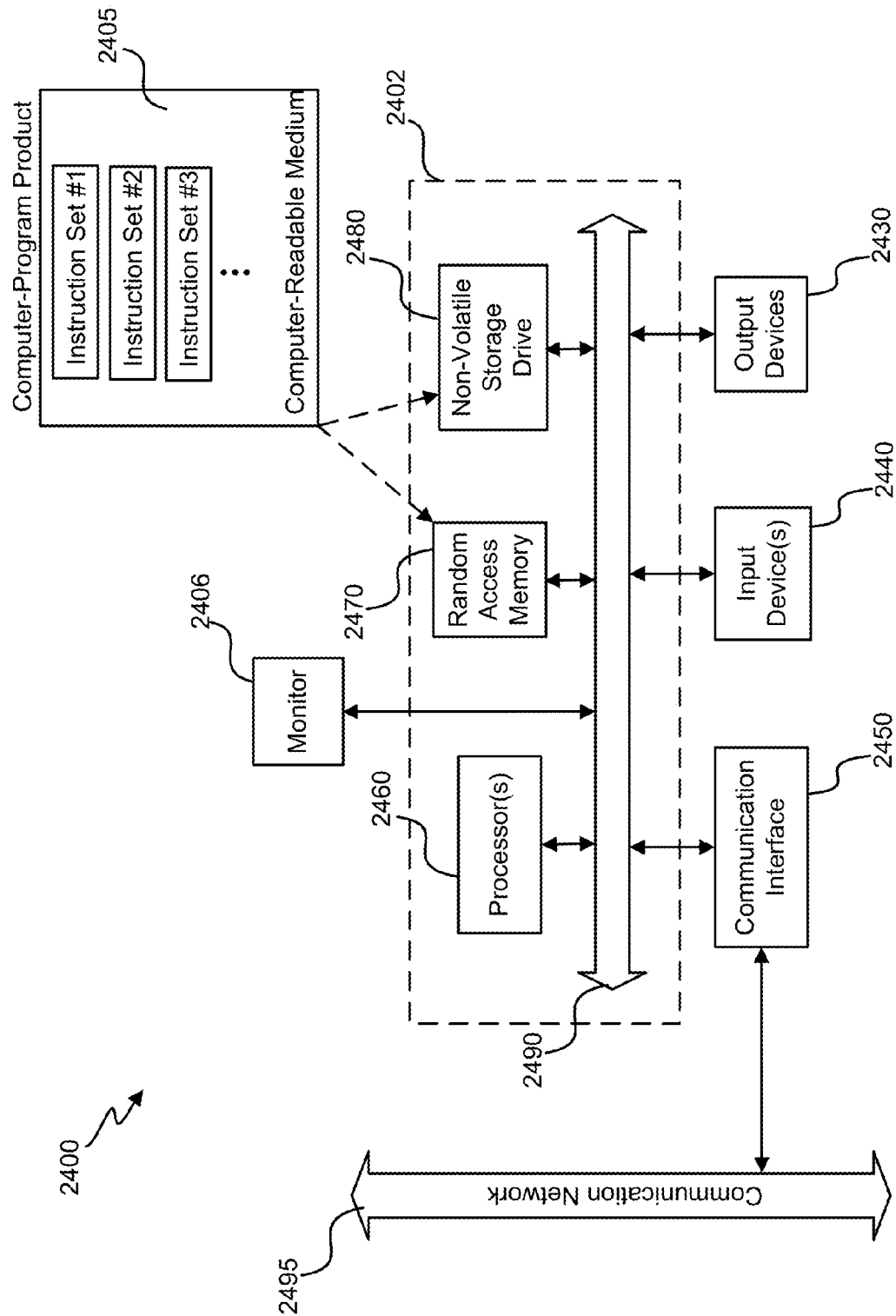
FIG. 24 is a block diagram of an embodiment of a special-purpose computer system for generating a user interface on a mobile device remote from a hazard detector.

FIG. 24 is a block diagram of an embodiment of a special-purpose computer system 2400 for generating a user interface on a mobile device remote from a hazard detector. The methods and systems described herein may be implemented by computer-program products that direct a computer system to perform the actions of the methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof.

Special-purpose computer system 2400 comprises a computer 2402, a monitor 2406 coupled to computer 2402, one or more additional user output devices 2430 (optional) coupled to computer 2402, one or more user input devices 2440 (e.g., keyboard, mouse, track ball, touch screen) coupled to computer 2402, an optional communications interface 2450 coupled to computer 2402, a computer-program product 2405 stored in a tangible computer-readable memory in computer 2402. Computer-program product 2405 directs system 2400 to perform the above-described methods. Computer 2402 may include one or more processors 2460 that communicate with a number of peripheral devices via a bus subsystem 2490. These peripheral devices may include user output device(s) 2430, user input device(s) 2440, communications interface 2450, and a storage subsystem, such as random access memory (RAM) 2470 and non-transitory storage drive 2480 (e.g., disk drive, optical drive, solid state drive), which are forms of tangible computer-readable memory.

Computer-program product 2405 may be stored in non-transitory storage drive 2480 or another computer-readable medium accessible to computer 2402 and loaded into memory 2470. Each processor 2460 may comprise a microprocessor, such as a microprocessor from Intel® or Advanced Micro Devices, Inc.®, or the like. To support computer-program product 2405, the computer 2402 runs an operating system that handles the communications of product 2405 with the above-noted components, as well as the communications between the above-noted components in support of the computer-program product 2405. Exemplary operating systems include Windows® or the like from Microsoft Corporation, Solaris® from Sun Microsystems, LINUX, UNIX, and the like.

User input devices 2440 include all possible types of devices and mechanisms to input information to computer system 2402. These may include a keyboard, a keypad, a mouse, a scanner, a digital drawing pad, a touch screen incorporated into the display, audio input devices such as voice recognition systems, microphones, and other types of input devices. In various embodiments, user input devices 2440 are typically embodied as a computer mouse, a trackball, a track pad, a joystick, wireless remote, a drawing tablet, a voice command system. User input devices 2440 typically allow a user to select objects, icons, text and the like that appear on the monitor 2406 via a command such as a click of a button or the like. User output devices 2430 include all possible types of devices and mechanisms to output information from computer 2402. These may include a display (e.g., monitor 2406), printers, non-visual displays such as audio output devices, etc.

Communications interface 2450 provides an interface to other communication networks and devices and may serve as an interface to receive data from and transmit data to other systems, WANs and/or the Internet 2318. Embodiments of communications interface 2450 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 2450 may be coupled to a computer network, to a FireWire® bus, or the like. In other embodiments, communications interface 2450 may be physically integrated on the motherboard of computer 2402, and/or may be a software program, or the like.

RAM 2470 and non-transitory storage drive 2480 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 2470 and non-transitory storage drive 2480 may be configured to store the basic programming and data constructs that provide the functionality of various embodiments of the present invention, as described above.

Software instruction sets that provide the functionality of the present invention may be stored in RAM 2470 and non-transitory storage drive 2480. These instruction sets or code may be executed by the processor(s) 2460. RAM 2470 and non-transitory storage drive 2480 may also provide a repository to store data and data structures used in accordance with the present invention. RAM 2470 and non-transitory storage drive 2480 may include a number of memories including a main random access memory (RAM) to store instructions and data during program execution and a read-only memory (ROM) in which fixed instructions are stored. RAM 2470 and non-transitory storage drive 2480 may include a file storage subsystem providing persistent (non-transitory) storage of program and/or data files. RAM 2470 and non-transitory storage drive 2480 may also include removable storage systems, such as removable flash memory.

Bus subsystem 2490 provides a mechanism to allow the various components and subsystems of computer 2402 to communicate with each other as intended. Although bus subsystem 2490 is shown schematically as a single bus, alternative embodiments of the bus subsystem may utilize multiple busses or communication paths within the computer 2402.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for adjusting a setting of a hazard detector on a mobile device remote from the hazard detector, the system comprising:

a user interface executed on the mobile device that accesses a computer server system via the Internet, the mobile device configured to:
   display a current value for the setting of the hazard detector, the current value indicating a value for the setting that is currently in effect on the hazard detector,
   receive user input indicating an adjustment to the setting, the adjustment to change the setting from the current value to an adjusted value,
   transmit the adjusted value to the computer server system via the Internet,
   display a pending indicator for the setting indicating that the adjusted value is not in effect on the hazard detector,
   receive a signal from the computer server system indicating that the adjusted value is in effect on the hazard detector, and
   display an indication of the setting such that the adjusted value is indicated as being in effect on the hazard detector;
the computer server system being communicatively coupled via the Internet to the mobile device and configured to:
   receive the adjusted value,
   determine that the adjusted value corresponds to the hazard detector,
   store the adjusted value while waiting for a check-in event from the hazard detector;
   after storing the adjusted value while waiting for the check-in event from the hazard detector, receive the check-in event from the hazard detector,
   transmit the adjusted value to the hazard detector in response to receiving the check-in event, and
   transmit the signal indicating that the adjusted value is in effect to the mobile device, wherein the computer server system is located remote from a structure at which the hazard detector is installed; and
the hazard detector, installed at the structure, being communicatively coupled with the Internet such that the hazard detector communicates with the computer server system via an Internet-connected router and the Internet, the hazard detector configured to:
   detect at least one of smoke and carbon monoxide (CO),
   transmit the check-in event to the computer server system after a time interval since transmitting a previous check-in event,
   receive the adjusted value, and
   apply the adjusted value to the setting.

2. The system of claim 1, further comprising:
a second user interface executed on a second mobile device, the second user interface being configured to:
   receive a second user input indicating a second adjustment to the setting, the second adjustment to change the setting to a second adjusted value, and
   transmit the second adjusted value to the computer server system;
the computer server system being communicatively coupled to the second mobile device and further configured to:
   receive the second adjusted value, and
   determine which of the adjusted value and the second adjusted value to transmit to the hazard detector.

3. The system of claim 2, wherein the computer server system determines which of the adjusted value and the second adjusted value to transmit by comparing a time indicating when the adjusted value is received with a second time indicating when the second adjusted value is received, and wherein a most recent adjusted value is transmitted to the hazard detector.

4. The system of claim 1, wherein:
the hazard detector is further configured to:
   receive a second user input indicating a second adjustment to the setting, the second adjustment to change the setting to a second adjusted value, and
   transmit the second adjusted value to the computer server system; and
the computer server system is further configured to:
   receive the second adjusted value, and
   determine which of the adjusted value and the second adjusted value to transmit to the hazard detector.

5. The system of claim 1, wherein the hazard detector is further configured to activate a light source at a brightness level corresponding to the adjusted value.

6. The system of claim 1, wherein the hazard detector is further configured to generate speech in a language corresponding to the adjusted value.

7. The system of claim 1, wherein the hazard detector is further configured to generate speech that announces a location corresponding to the adjusted value, the location indicating a room that the hazard detector is located in.

8. A method for adjusting a setting of a hazard detector on a mobile device remote from the hazard detector, the method comprising:
   displaying a list of settings for the hazard detector, the hazard detector being configured to detect at least one of smoke and carbon monoxide (CO);
   receiving a first user input selecting the setting from the list of settings;
   expanding a display area for the setting in response to receiving the first user input;
   displaying a current value for the setting in the expanded display area, the current value indicating a value for the setting that is currently in effect on the hazard detector;
   receiving a second user input indicating an adjustment to the setting, the adjustment to change the setting from the current value to an adjusted value, wherein the adjusted value corresponds to an ancillary feature of the hazard detector that is distinct from alarm functionality triggered by either smoke and carbon monoxide detection;
   transmitting the adjusted value from the mobile device to a computer server system via the Internet;
   storing the adjusted value by the computer server system while waiting for a check-in event from the hazard detector;
   transmitting a check-in event from the hazard detector to the computer server system via the Internet, after transmitting the adjusted value from the mobile device to the computer server system, wherein the hazard detector is located at a structure remote from a location of the computer server system;
   transmitting the adjusted value from the computer server system to the hazard detector via the Internet after transmitting the check-in event from the hazard detector to the computer server system; and
   applying the adjusted value to the setting on the hazard detector.

9. The method of claim 8, further comprising:
   detecting motion at the hazard detector; and
   determining, based on the adjusted value, whether a light source of the hazard detector is to be activated in response to detecting motion.

10. The method of claim 7, further comprising:
detecting an ambient light level at the hazard detector that is less than a threshold; and
determining, based on the adjusted value, whether a light source of the hazard detector is to be activated in response to detecting the ambient light level.

11. The method of claim 7, further comprising:
detecting an increase in humidity level at the hazard detector; and
determining, based on the adjusted value, whether a smoke threshold of the hazard detector is adjusted in response to detecting the increase, the smoke threshold indicating a level of detected smoke at which an alert of the hazard detector is activated.

12. The method of claim 7, further comprising:
detecting that a primary power source of the hazard detector is supplying power; and
determining, based on the adjusted value, whether an indicator of the hazard detector is activated in response to detecting that the primary power source is supplying power.

13. The method of claim 7, further comprising:
detecting a hazard level that is greater than a pre-alarm threshold and less than an alarm threshold, the hazard level indicating an amount of smoke or CO; and
determining, based on the adjusted value, whether an alert of the hazard detector is activated in response to detecting the hazard level.

14. The method of claim 7, further comprising:
detecting a specific motion at the hazard detector; and
determining, based on the adjusted value, whether an alert of the hazard detector is deactivated in response to detecting the specific motion.

15. A non-transitory computer-readable medium, having instructions stored therein, which when executed cause a computer to perform a set of operations comprising:
displaying a list of settings for a hazard detector, the hazard detector being configured to detect at least one of smoke and carbon monoxide (CO);
receiving a first user input selecting a first setting from the list of settings;
expanding a first display area for the first setting in response to receiving the first user input;
displaying a first current value for the first setting in the expanded first display area, the first current value indicating a value for the first setting that is currently in effect on the hazard detector;
receiving a second user input selecting a second setting from the list of settings;
reducing the first display area for the first setting in response to receiving the second user input;
expanding a second display area for the second setting in response to receiving the second user input;
displaying a second current value for the second setting in the expanded second display area, the second current value indicating a value for the second setting that is currently in effect on the hazard detector, wherein the first current value and the second current value correspond to ancillary features of the hazard detector that are distinct from one or more alarm features corresponding to either smoke or carbon monoxide detection;
receiving a third user input indicating an adjustment to the second setting, the adjustment to change the second setting from the second current value to an adjusted value;
displaying a pending indicator for the second setting indicating that the adjusted value is not in effect on the hazard detector;
transmitting the adjusted value to a computer server system via the Internet, wherein the computer server system is located remote from a structure at which the hazard detector is located;
receiving a signal from the computer server system indicating that the adjusted value for the second setting is in effect on the hazard detector; and
removing the pending indicator in response to receiving the signal.

16. The non-transitory computer-readable medium of claim 15, having further instructions stored therein, which when executed cause the computer to perform a set of operations comprising:
displaying a replacement date for the hazard detector, the replacement date indicating a date by which the hazard detector should be replaced with a new hazard detector.

17. The non-transitory computer-readable medium of claim 15, having further instructions stored therein, which when executed cause the computer to perform a set of operations comprising:
displaying a media access control address of the hazard detector.

18. The non-transitory computer-readable medium of claim 15, having further instructions stored therein, which when executed cause the computer to perform a set of operations comprising:
displaying a wireless internet protocol address of the hazard detector.

19. The non-transitory computer-readable medium of claim 15, having further instructions stored therein, which when executed cause the computer to perform a set of operations comprising:
displaying a model number or serial number of the hazard detector.

20. The system of claim 1, wherein the adjusted value transmitted by the mobile device to the computer server system via the Internet and subsequently transmitted by the computer server system to the hazard detector via the Internet adjusts an ancillary feature of the hazard detector that is distinct from an alarm activated based on either smoke and carbon monoxide detection.

* * * * *